US007482006B2

(12) United States Patent
Chang et al.

(10) Patent No.: US 7,482,006 B2
(45) Date of Patent: Jan. 27, 2009

(54) RECOMBINANT ENTEROVIRUS 71 NEUTRALIZING ANTIBODIES AND APPLICATIONS THEREOF

(75) Inventors: Tse-Wen Chang, Xizhi (TW); Jim Jinn-Chyuan Sheu, Xizhi (TW); Lee-Hwa Lo, Xizhi (TW); Nien-Yi Chen, Sindinn (TW); Young-Sun Lin, Xizhi (TW)

(73) Assignee: Development Center for Biotechnology (TW)

( * ) Notice: Subject to any disclaimer, the term of this patent is extended or adjusted under 35 U.S.C. 154(b) by 0 days.

(21) Appl. No.: 11/404,770

(22) Filed: Apr. 17, 2006

(65) Prior Publication Data

US 2006/0257859 A1 Nov. 16, 2006

(30) Foreign Application Priority Data

May 11, 2005 (CN) ................................ 94 1 15151

(51) Int. Cl.
*A61K 39/42* (2006.01)
*C12P 21/08* (2006.01)
*C12N 15/13* (2006.01)
*C07K 16/10* (2006.01)

(52) U.S. Cl. ................. 424/147.1; 530/388.3; 435/69.6

(58) Field of Classification Search ..................... 435/5, 435/345, 320.1; 424/204.1, 93.2
See application file for complete search history.

(56) References Cited

U.S. PATENT DOCUMENTS

2006/0099205 A1* 5/2006 Adams et al. ............ 424/133.1
2006/0292693 A1* 12/2006 Yen et al. .................... 435/345

OTHER PUBLICATIONS

Tan et al., "High-tired neutralizing antibodies to human enterovirus 71 preferentially bind to the N-terminal portion of the capsid protein," Arch Virol (2007).*
Wei Foo et al., "Identification of neutralizing linear epitopes from the VP1 capsid protein of Enterovirus 71 using synthetic peptides," Virus Research 125, pp. 61-68 (2007).*
See Result 9, Score search results (2007).*
See Result 2, NCBI Blast search of Seq Id No. 26 (2007); see also Rhyner et al., "Phage display of human antibodies from a patient suffering from coeliac disease and selection of isotype-specific scFV against gliadin," Immunology, 110, pp. 269-274 (2003).*
Rudikoff et al (Proc Natl Acad Sci USA 79: 1979-1983, 1982).*
Amit et al, Science 233: 747-753, 1986.*
Yu et al (Journal of Biomedical Science 7:523-528, 2000).*
Rigonan et al (Journal of Clinical Microbiology 36:1877-1881, 1998).*
Hsueh et al (Modern Pathology 13:1200-1205, 2000).*
Hsiung et al (Journal of Microbiology, Immunology, and Infection 33:1-8, 2000).*
Sai Kit Lam, "Southeast Asia Update," *Emerging Infectious Diseases,* vol. 4, No. 2, Apr.-Jun. 1998, pp. 145-147.
Trong-Neng Wu et al., "Sentinel Surveillance for Enterovirus 71, Taiwan, 1998," *Emerging Infectious Diseases,* vol. 5, No. 3, May-Jun. 1999, pp. 458-460.
Shih-Min Wang et al., "Clinical Spectrum of Enterovirus 71 Infection in children in Southern Taiwan, with an Emphasis on Neurological Complication," *CID,* 1999, pp. 184-190.
Hiroshi Komatsu, MD et al., "Outbreak of Severe Neurologic Involvement Associated with Enterovirus 71 Infection," *Pediatric Neurology.,* vol. 20, No. 1, 1999, pp. 17-23.
Isao Hashimoto et al., "Pathogenicity Of A Poliomyelitis-Like Disease In Monkeys Infected Orally With Enterovirus 71: A Model For Human Infection," *Neuropathology and Applied Neurobiology,* 1982, pp. 149-156.
I. Hashimoto et al., "Comparative Studies on the Neurovirulence of temperature-sensitive and Temperature-resistance Viruses of Enterovirus 71 in Monkeys," *Acta Neuropathol* (*Berl*), 1983, pp. 266-270.
R. G. H. Cotton et al., "Fusion of Two Immunoglobulin-Producing Myeloma Cells," *Medical Research Council,* vol. 244, 1973, pp. 42-43.
Martin J. Glennie et al., "Clinical Trials of Antibody Therapy," *Immunology Today,* vol. 21, No. 8, pp. 403-410, date not available.
Richard Malley et al., "Reduction of Respiratory Syncytial Virus (RSV) in Tracheal Aspirates in Intubated Infants by Use of Humanized Monoclonal Antibody to RSV F Protein," *The Journal of Infectious Diseases,* 1998, pp. 1555-1561.
Albert Marchetti et al., "Impact of Palivizumab on Expected Costs of Respiratory Syncytial Virus Infection in Preterm Infants: Potential for Savings," *Clinical Therapeutics,* vol. 21, No. 4, 1999, pp. 752-766.
Graham Fox et al., "The Cell Attachment Site on Foot-and-Mouth Disease Virus Includes the Amino Acid Sequence RGD (Arginine-Glycine-Aspartic Acid)," *J. gen. Virol.,* 1989, pp. 625-637.

(Continued)

*Primary Examiner*—Mary E Mosher
(74) *Attorney, Agent, or Firm*—Harness, Dickey & Pierce, P.L.C.

(57) ABSTRACT

Provided is an antibody against enterovirus 71 comprising the amino acid sequence shown in SEQ ID NOS: 14, 15, 16, 17, 18, 19, 20, 21, 22, 23, 24, 25, or 26 or functionally active homologues thereof. Also provided are methods for obtaining the antibody comprising (a) selecting a yeast expressing such an antibody from a yeast library, (b) culturing the yeast under conditions that the antibody is expressed, and (c) recovering the antibody from the culture. Also provided is a process for producing the antibody comprising (a) culturing a host cell under conditions that the antibody is expressed, (b) recovering the antibody from the culture, wherein the host cells are transformed or transfected for expressing the antibody against enterovirus 71. Also provided are pharmaceutical compositions comprising an antibody against enterovirus 71 and a pharmaceutically acceptable carrier or diluent, wherein the antibody has an anti-virus agent or detectable label attached thereto.

15 Claims, 11 Drawing Sheets

OTHER PUBLICATIONS

E. Pfaff et al., "Analysis of Neutralizing Epitopes on Foot-and-Mouth Disease Virus," *J. of Virology,* 1988, pp. 2033-2040.

Philip D. Minor et al., "Antigenic Structure of Polioviruses of Serotypes 1, 2 and 3," *J. gen. Virol.,* 1986, pp. 1283-1291.

Timo Hyypia et al, "Classification of enteroviruses based on molecular and biological properties," *J. gen. Virol.,* 1997, pp. 1-11.

Cheng-Nan Wu et al., "Protection against lethal enterovirus 71 infection in newborn mice by passive immunization with submit VP1 vaccines and inactivated virus," *Vaccine,* 2002, pp. 895-904.

Jen-Ren Wang et al., "Change of Major Genotype of Enterovirus 71 in Outbreaks of Hand-Foot-and-Mouth Disease in Taiwan between 1998 and 2000," *J. of Clinical Mircobiology,* vol. 40, No. 1, 2000, pp. 10-15.

Shin-Ru Shih et al., "Genetic Analysis of Enterovirus 71 isolated from fatal and non-fatal cases of hand, foot and mouth disease during an epidemic in Taiwan, 1998," *Virus Research,* 2000, pp. 127-136.

Tristan J. Vaughan et al., "Human antibodies by design," *Nature Biotechnology,* vol. 16, 1998, pp. 535-539.

Abraham Karpas et al., "A human myeloma cell line suitable for the generation of human monoclonal antibodies," *PNAS,* vol. 98, No. 4, 2001, pp. 1799-1804.

* cited by examiner

Fig. 1.

A. The DNA-BD/EV71 vp1 protein binds to the GAL1 upstream activating sequence (UAS) but cannot activate transcription without the AD.

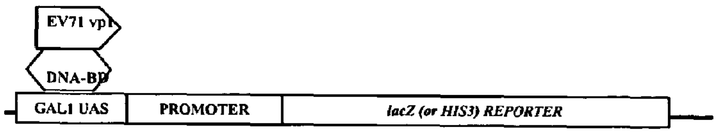

B. The AD/scFv library protein cannot localize to the UAS and thus does not activate transcription.

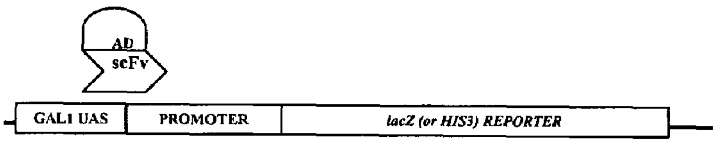

C. Interaction between the EV71 vp1 and scFv library encoded regions of the two hybrid proteins reconstitutes GAL4 function and results in reporter gene expression.

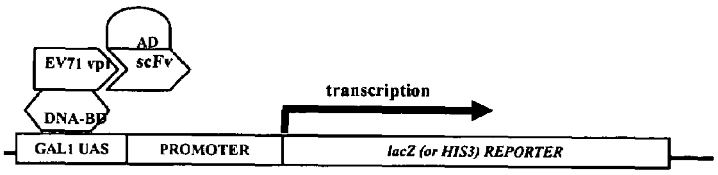

Fig. 2.
Paretal Clons of G338, G235 and G234
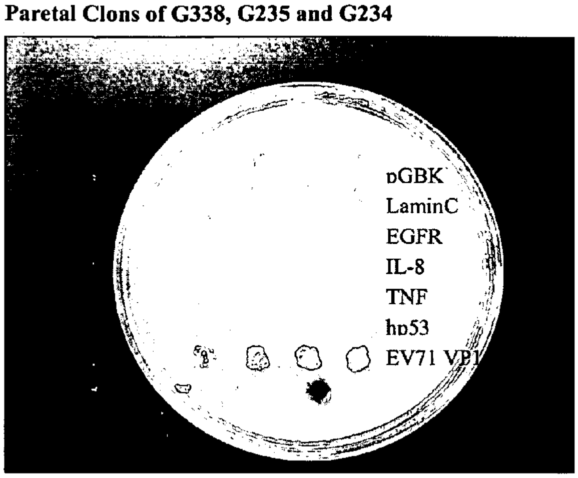
Paretal Clone of G333, G334, G335 and G336
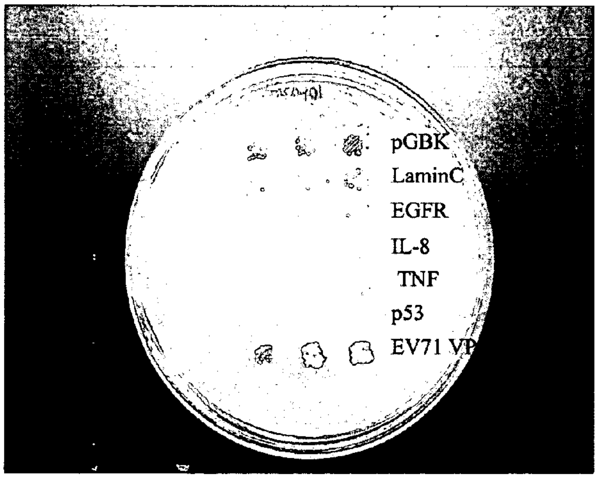
Paretal Clone of G621, G622, G623, G624 and G625
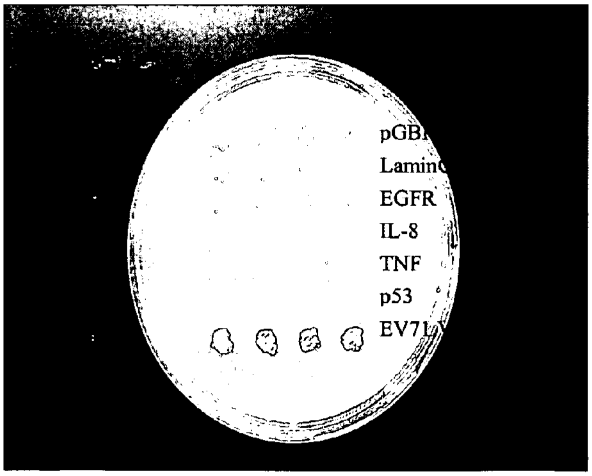

FIG. 6

| Antigen | Selected scFv (200nM for coupling on a Ni-NTA chip) | | | | | | | | |
|---|---|---|---|---|---|---|---|---|---|
| GST-VP1 | G621 | G622 | G623 | G624 | G625 | G333 | G334 | G335 | G336 |
| 50nM | 19 | 16 | 20 | | 21 | 14 | 20 | 12 | 19 |
| 100nM | 33 | 28 | 35 | 29 | 37 | 27 | 29 | 20 | 27 |
| 200nM | 58 | 48 | 68 | 53 | 60 | 49 | 48 | 34 | 43 |
| 500nM | 143 | 123 | 116 | 136 | 126 | 100 | 104 | 82 | 112 |
| 1000nM | 261 | 228 | 200 | | 217 | 184 | 198 | 153 | 161 |
| 1/[S] | | | | | | | | | |
| 0.001 | 0.0038 | 0.0044 | 0.0050 | | 0.0046 | 0.0054 | 0.0051 | 0.0065 | 0.0062 |
| 0.002 | 0.0070 | 0.0081 | 0.0086 | 0.0074 | 0.0079 | 0.0100 | 0.0096 | 0.0122 | 0.0089 |
| 0.005 | 0.0172 | 0.0208 | 0.0147 | 0.0189 | 0.0167 | 0.0204 | 0.0208 | 0.0294 | 0.0233 |
| 0.01 | 0.0303 | 0.0357 | 0.0286 | 0.0345 | 0.0270 | 0.0370 | 0.0345 | 0.0500 | 0.0370 |
| 0.02 | 0.0526 | 0.0625 | 0.0500 | | 0.0476 | 0.0714 | 0.0500 | 0.0833 | 0.0526 |
| **Kd (nM)** | **654.6** | **655.9** | **580.9** | **ud** | **342.2** | **1064.9** | **1077.3** | **1722.6** | **1127.5** |

RU (brace for rows 50nM–1000nM)

FIG. 7.
(A)
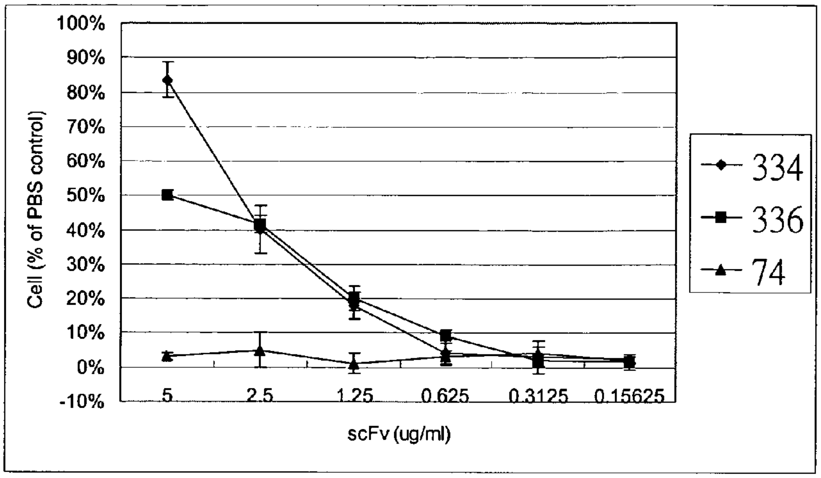
(B)
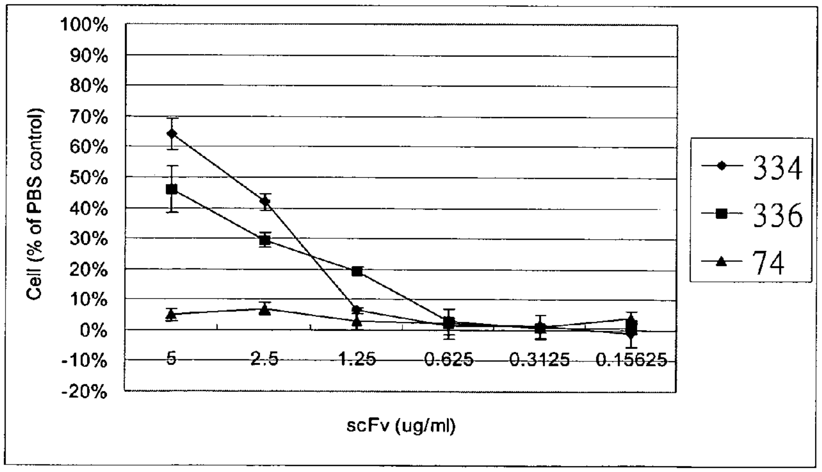

| ScFv | Test-1 | Test-2 | Avg. | % PBS | SD% |
|---|---|---|---|---|---|
| | plaques | plaques | plaques | | |
| 621 | 39 | 36 | 37.5 | 71% | 2% |
| 622 | 54 | 42 | 48 | 91% | 8% |
| 623 | 42 | 37 | 39.5 | 75% | 3% |
| 625 | 33 | 43 | 38 | 72% | 7% |
| 333 | 57 | 42 | 49.5 | 93% | 10% |
| 334 | 61 | 34 | 47.5 | 90% | 18% |
| 335 | 42 | 46 | 44 | 83% | 3% |
| 336 | 48 | - | 48 | 91% | - |
| PBS | - | 53 | 53 | 100% | - |

(B)

| ScFv | Test-1 | Test-2 | Avg. | % PBS | SD% |
|---|---|---|---|---|---|
| | plaques | plaques | plaques | | |
| 621 | 16 | 18 | 17 | 47% | 4% |
| 622 | 22 | 21 | 21.5 | 60% | 2% |
| 623 | 34 | 18 | 31 | 72% | 31% |
| 625 | 32 | 23 | 27.5 | 76% | 18% |
| 333 | 29 | 18 | 23.5 | 65% | 22% |
| 334 | 29 | 26 | 27.5 | 76% | 6% |
| 335 | 20 | 22 | 21 | 58% | 4% |
| 336 | 15 | - | 15 | 42% | - |
| PBS | - | 36 | 36 | 100% | - |

(A)

FIG. 9
(B)
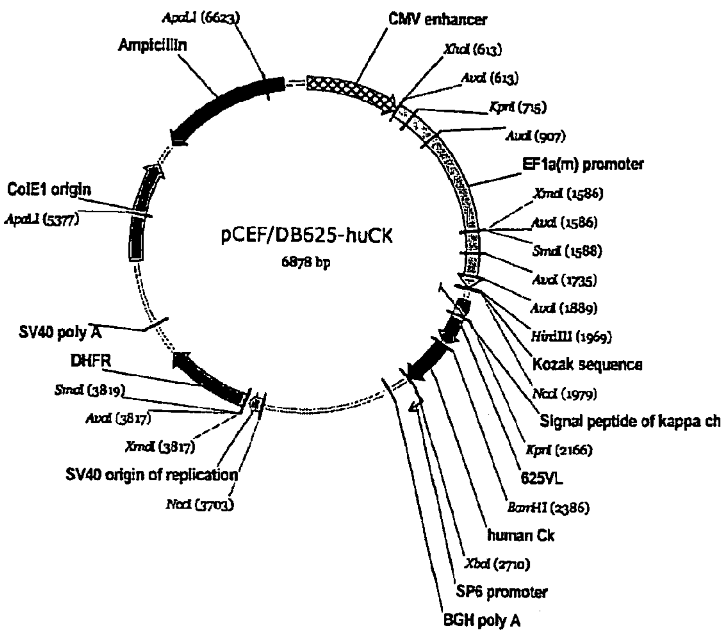
(C)
pAcDB3 Baculovirus Transfer Vector
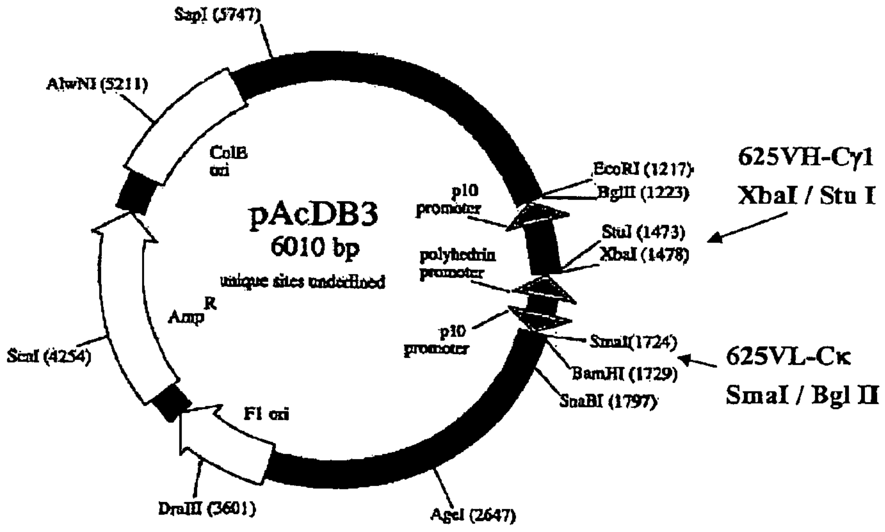

FIG. 10
(A)
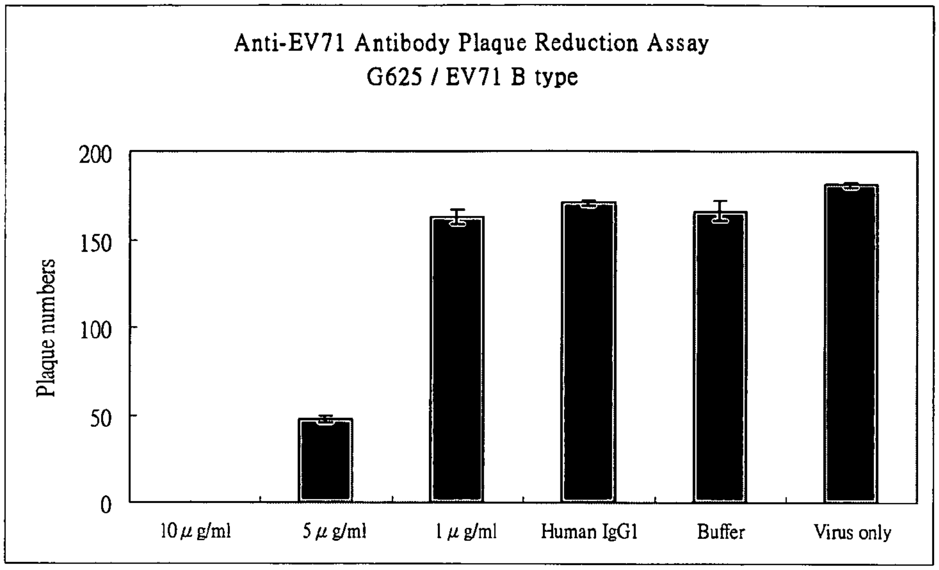
(B)
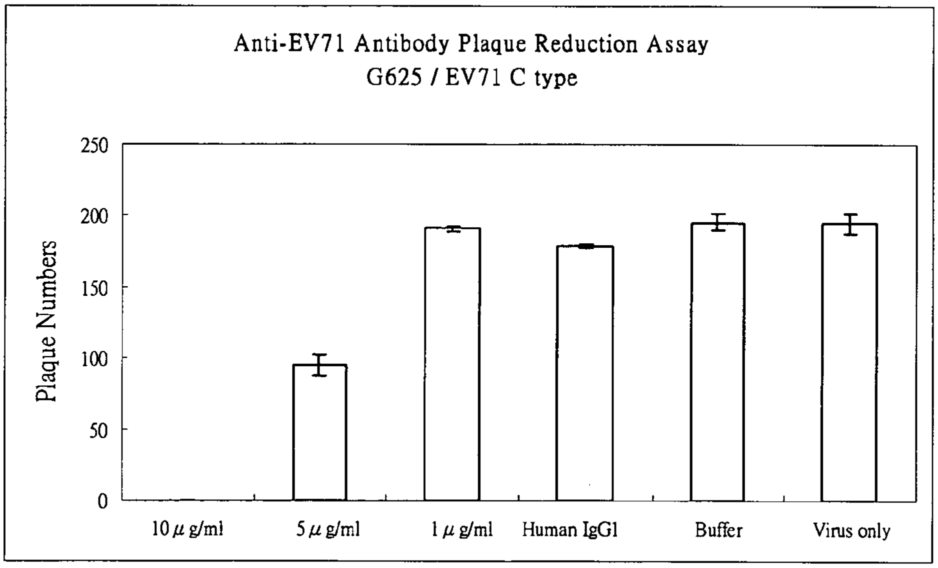

SEQUENCE LISTING

<160> NUMBER OF SEQ ID NOS: 34

<210> SEQ ID NO 1
<211> LENGTH: 759
<212> TYPE: DNA
<213> ORGANISM: Artificial
<220> FEATURE:
<223> OTHER INFORMATION: Synthetically generated sequence (V_region)

<400> SEQUENCE: 1
gaggtgcagc tggtggagtc cgggggaggc ttgatccagc ctgggggtc cctgagactc 60 tcctgtggag cctctggatt cacctttagt acctcttgga tggcctgggt ccgccaggct 120
ccagggaagg ggctggagtg ggtggccacc ataggccaag atggaagcca gcaatactat 180
gcggactctg tgaagggccg attcaccgtc tccagagaca acgccaagaa ctcactgtgt 240
ctgcaaatga acagcctgag agccgaggac acggctgttt attactgtgc gagagctctt 300
gacgacagtg ctggctggtt tgaatttgac ttctggggcc agggaaccct ggtcaccgtc 360
tcctcaggcg gtggcggatc aggcggcgga ggatctggcg gaggtggcag cggcggtgga 420
ggcagtaatt ttacgccgac tcagccccac tctgtgtcgg aggctccggg gaggacggtc 480
accatctcct gcactgggag cagctccaac atcggggcag gttatgatgt acactggtac 540
cagcagcttc caggatcagc ccccaatgtc ctcatctatg gtaacagcaa tcggccctca 600
ggggtccctg accgattctc tggccccaag tctggcaccc cagcctcccc ggccatcact 660
gcattccagg ctgaggatga ggctgattat tactgccagt cgtatgacag cagcctgagt 720
ggtgaggtct tcggcggggg cacccagctg accgtcctc 759

<210> SEQ ID NO 2
<211> LENGTH: 789
<212> TYPE: DNA
<213> ORGANISM: Artificial
<220> FEATURE:
<223> OTHER INFORMATION: Synthetically generated sequence (V_region)

<400> SEQUENCE: 2
gaggtgcagc tggtggagtc cgggggaggc ttgatccagc ctgggggtc cctgagactc 60 tcctgtggag cctctggatt cacctttagt acctcttgga tggcctgggt ccgccaggct 120
ccagggaagg ggctggagtg ggtggccacc ataggccaag atggaagcca gcaatactat 180
gcggactctg tgaagggccg attcaccgtc tccagagaca acgccaagaa ctcactgtat 240
ctgcaaatga acagcctgag agccgaggac acggctgttt attactgtgc gagagctctt 300

-continued

```
gacgacagtg ctggctggtt tgaatttgac ttctggggcc agggaaccct ggtcaccgtc    360
tcctcaggcg gtggcggatc aggcggcgga ggatctggcg gaggtggcag cggcggtgga    420
ggcagtaatt ttacgctgac tcagccccac tctgtgtcgg aggctccggg gaggacggtc    480
accatctcct gcactgggag cagctccaac atcggggcag gttatgatgt acactggtac    540
cagcagcttc caggatcagc ccccaaagtc ctcacctatg gtaacagcaa tcggccctca    600
ggggtccctg accgattctc tggctccaag tctggcaccc cagcctcccc ggccatcact    660
gcattccagg ctgaggatga ggctgattat tactgccagt cgtatgacag cagcctgagt    720
ggtgaggtct tcggcggggg cacccagctg accgtcctcc cgaattcgag cacccagctg    780
accgtcctc                                                            789
```

<210> SEQ ID NO 3
<211> LENGTH: 759
<212> TYPE: DNA
<213> ORGANISM: Artificial
<220> FEATURE:
<223> OTHER INFORMATION: Synthetically generated sequence (V_region)

<400> SEQUENCE: 3

```
gaggtgcagc tggtggagtc cgggggaggc ttgatccagc ctgggggggtc cctgagactc     60
tcctgtggag cctctggatt cacctttagt acctcttgga tggcctgggt ccgccaggct    120
ccagggaagg ggctggagtg ggtggccacc ataggccaag atggaagcca gcaatactat    180
gcggactctg tggagggccg attcaccgtc tccagagaca acgccaagaa ctcactgtat    240
ctgcaaatga acagcctgag agccgaggac acggctgttt attactgtgc gagagctctt    300
gacgacagtg ctggctggtt tgaatttgac ttctggggcc agggaaccct ggtcaccgtc    360
tcctcaggcg gtggcggatc aggcggcgga ggatctggcg gaggtggcag cggcggtgga    420
ggcagtaatt ttacgctgac tcagccccac tctgtgtcgg aggccccggg gaggacggtc    480
accatctcct gcactgggag cagctccaac atcggggcag gttatgatgt acactggtac    540
cagcagcctc caggatcagc ccccaaagtc ctcacctatg gtaacagcaa tcggccctca    600
ggggtccctg accggttctc tggctccaag tctggcacct cagcctcccc ggccatcact    660
gcattccagg ccgaggatga ggctgatcat tactgccagt cgtatgacag cagcctgagt    720
ggtgaggcct tcggcggggg cacccagctg accgtcctc                           759
```

<210> SEQ ID NO 4
<211> LENGTH: 759
<212> TYPE: DNA
<213> ORGANISM: Artificial
<220> FEATURE:
<223> OTHER INFORMATION: Synthetically generated sequence (V_region)

<400> SEQUENCE: 4

```
gaggtgcagc tggtggagtc cgggggaggc ttgatccagc ctgggggggtc cctgagactc     60
tcctgtggag cctctggatt cacctttagt acctcttgga tggcctgggt ccgccaggct    120
ccagggaagg ggctggagtg ggtggccacc ataggccaag atggaagcca gcaatactat    180
gcggactctg tgaagggccg attcaccgtc tccagagaca acgccaagaa ctcactgtat    240
ctgcaaatga acagcctgag agccgaggac acggctgttt attactgtgc gagagctctt    300
gacgacagtg ctggctggtt tgaatttgac ttctggggcc agggaaccct ggtcaccgtc    360
tcctcaggcg gtggcggatc aggcggcgga ggatctggcg gaggtggcag cggcggtgga    420
```

-continued ggcagtaatt ttacgctgac tcagccccac tctgtgtcgg aggctccggg gaggacggtc 480
accatctcct gcactgggag cagctccaac atcggggcag gttatgatgt acactggtac 540
cagcagcttc caggatcagc ccccaaagtc ctcatctatg gtaacagcaa tcggccctca 600
ggggtccctg accgattctc tggctccaag tctggcacct cagcctccct ggccatcact 660
gcattccagg ctgaggatga ggctgattat tactgccagt cgtatgacag cagcctgagt 720
ggtgaggtct tcggcggggg cacccagctg accgtcctc 759

<210> SEQ ID NO 5
<211> LENGTH: 759
<212> TYPE: DNA
<213> ORGANISM: Artificial
<220> FEATURE:
<223> OTHER INFORMATION: Synthetically generated sequence (V_region)

<400> SEQUENCE: 5
gaggtgcagc tggtggagtc cgggggaggc ttgatccagc ctggggggtc cctgagactc 60
tcctgtggag cctctggatt cacctttagt acctcttgga tggcctgggt ccgccaggct 120
ccagggaagg ggctggagtg ggtggccacc ataggccaag atggaagtca gcaatactat 180
gcggactctg tgaagggccg attcaccgtc tccagagaca acgccaagaa ctcactgtat 240
ctgcaaatga acagcctgag agccgaggac acggctgttt attactgtgc gagagctctt 300
gacgacagtg ctggctggtt tgaatttgac ttctggggcc cgggaaccct ggtcaccgtc 360
tcctcaggcg gtggtggacc aggcggcgga ggatctggcg gaggtggcag cggtggtgga 420
ggcagcgatt ttatgctgac tcagccccac tctgtgtcgg aggctccggg gaagacggtc 480
accatctcct gcactgggag cagctccaac atcggggcag gttatgatgt acactggtac 540
cagcagcttc caggatcagc ccccaaagtc ctcatctatg gtaacagcaa tcggccctca 600
ggggtccctg accgattctc tggctccaag tctggcacct cagcctcccc ggccatcact 660
gcattccagg ctgaggatga ggctgattat tactgccagt cgtatgacag cagcctgagt 720
ggtgtggtct tcggcggagg cacccagctg accgtcctc 759

<210> SEQ ID NO 6
<211> LENGTH: 768
<212> TYPE: DNA
<213> ORGANISM: Artificial
<220> FEATURE:
<223> OTHER INFORMATION: Synthetically generated sequence (V_region)

<400> SEQUENCE: 6
caggtccagc tggtgcagtc tggggctgag gtgaagaagc ctgggtcctc ggtgaaggtc 60
tcctgcaagg cctctggagg ccccctcagc gactatggct tcagctgggt gcgactggcc 120
cctggacaag ggcttgagtg ggtgggaggg atcatcccta tgtttggaac accaaactac 180
gcacagaagt ttcagggcgg agtctcgatt accgcggacg agtccacgac cactgcctac 240
atggagctga gcagcctgag atctgaggac acgggcgtgt attattgtgc gggacgaagc 300
ccagacgatt attttggttc tcgtcgggac aactatcact acgggataga cgtctggggc 360
caagggacca cggtcaccgt ctcctcaggc agtggtggat caggcggcgg aggatctggc 420
ggaggtggca gcggtggtgg aggcagtgaa attgtgatga cgcagtctcc atcctcattg 480
tctgcatctg taggaggcag agtcaccatc acgtgtcggg cgagtcaggg cattggcaat 540
tatttagcct ggtttcagca gaaaccaggg aaagccccta agcccctgat ctttgctgca 600
tccaacttgc aaagtggggt cccatcaagg ttcagcggcg gtggatctgg gacagaattc 660

-continued

```
actctcacca tcaccggcct gcagcctgaa gattttgcaa cttattactg ccaacagtat    720

aattattacc ctcccacttt cggcggaggg accaaggtgg aaatcaaa                 768


<210> SEQ ID NO 7
<211> LENGTH: 759
<212> TYPE: DNA
<213> ORGANISM: Artificial
<220> FEATURE:
<223> OTHER INFORMATION: Synthetically generated sequence  (V_region)

<400> SEQUENCE: 7

gaggtgcagc tggtggagtc cgggggaggc ttgatccagc ctggggggtc cctgagactc     60

tcctgtgtag cctctggatt cacctttagt acctcttgga tgacctgggt ccgccaggct    120

ccagggaagg ggctggagtg ggtggccacc ataggccaag atggaagtca gcaatactat    180

gtggactctg tgaagggccg attcaccgtc tccagagaca acgccaagaa ctcactgtat    240

ctgcaaatga acagcctgag agccgaggac acggctgttt attactgtgc gagagctctt    300

gacgacagtg ctggctggtt tgaatttgac ttctggggcc agggaaccct ggtcaccgtc    360

tcctcaggcg gtggtggatc aggcggcgga ggatctggcg gaggtggcag cggtggtgga    420

ggcagtaatt ttatgctgac tcagccccac tctgtgtcgg aggctccggg gaagacggtc    480

accatctcct gcactgggag cagctccaac atcggggcag gttatgatgt acactggtac    540

cagcagcttc caggatcagc ccccaaagtc ctcatctatg gtaacaacaa tcggccctca    600

ggggtccctg accgattctc tgactccaag tctggcacct cagcctccct ggccatcact    660

gcattccagg ctgaggatga ggctgattat tactgccagt cgtatgacag cagcctgagt    720

ggtgtggtct tcggcggagg cacccagctg accgtcctc                           759


<210> SEQ ID NO 8
<211> LENGTH: 759
<212> TYPE: DNA
<213> ORGANISM: Artificial
<220> FEATURE:
<223> OTHER INFORMATION: Synthetically generated sequence  (V_region)

<400> SEQUENCE: 8

gaggtgcagc tggtggagtc cgggggaggc ttgatccagc ctggggggtc cctgagactc     60

tcctgtggag cctctggatt cacctttagt acctcttgga tgacctgggt ccgccaggct    120

ccagggaagg ggctggagtg ggtggccacc ataggcccag atggaagtca gcaatactat    180

gtggactctg tgaagggccg attcaccgtc tccagagaca acgccaagaa ctcactgtat    240

ctgcaaatga acagcctgag agccgaggac acggctgttt attactgtgc gagagctctt    300

gacgacagtg ctggctggtt tgaatttgac ttctggggcc agggaaccct ggtcaccgtc    360

tcctcaggcg gtggtggatc aggcggcgga ggatctggcg gaggtggcag cggtggtgga    420

ggcagtaatt ttatgctgac tcaaccccac tctgtgtcgg aggctccggg gaagacggtc    480

accatctcct gcactgggag cagctccaac atcggggcag gttatgatgt acactggtac    540

cagcagcttc caggatcagc ccccaaagtc ctcatctatg gtaacaacaa tcggccctca    600

ggggtccctg accgattctc tggctccaag tctggcacct cagcctccct ggccatcact    660

gcattccagg ctgaggatga ggctgattat tactgccagt cgtatgacag cagcctgagt    720

ggtgtggtct tcggcggagg cacccagctg accgtcctc                           759


<210> SEQ ID NO 9
```

-continued

<211> LENGTH: 759
<212> TYPE: DNA
<213> ORGANISM: Artificial
<220> FEATURE:
<223> OTHER INFORMATION: Synthetically generated sequence (V_region)

<400> SEQUENCE: 9

```
gaggtgcagc tggtggagtc cgggggaggc ttgatccagc ctgggggtc cctgagactc      60

tcctgtggag cctctggatt cacctttagt acctcttgga tgacctgggt ccgccaggct    120

ccagggaagg ggctggagtg ggtggccacc ataggccaag atggaagtca gcaatactat    180

gcggactctg tgaagggccg attcaccgtc tccagagaca acgccaagaa ctcactgtat    240

ctgcaaatga acagcctgag agccgaggac acggctgttt attactgtgc gagagctctt    300

gacgacagtg ctggctggtt tgaatttgac ttctggggcc agggaaccct ggtcaccgtc    360

tcctcaggcg gtggtggatc aggcggcgga ggatctggcg gaggtggcag cggtggtgga    420

ggcagtaatt ttatgctgac tcagccccac tctgtgtcgg aggctccggg gaagacggtc    480

accatctcct gcactgggag cagctccaac atcggggcag gttatgatgt acactggtac    540

cagcagcttc caggatcagc cccaaagtc ctcatctatg gtaacaacaa tcggccctca    600

ggggtccctg accgattctc tggctccaag tctggcacct cagcctccct ggccatcact    660

gcattccagg ctgaggatga ggctgattat tactgccagt cgtatgacag cagcctgagt    720

ggtgtggtct tcggcggagg cacccagctg accgtcctc                          759
```

<210> SEQ ID NO 10
<211> LENGTH: 768
<212> TYPE: DNA
<213> ORGANISM: Artificial
<220> FEATURE:
<223> OTHER INFORMATION: Synthetically generated sequence (V_region)

<400> SEQUENCE: 10

```
caggtccagc tggtgcagtc tggggctgag gtgaagaagc ctgggtcctc ggtgaaggtc     60

tcctgcaagg cctctggagg ccccctcagc gactatggtt tcagctgggt gcgactggcc    120

cctggacaag ggcttgagtg ggtgggaggg atcatcccta tgtttggaac accaaactac    180

gcacagaagt ttcagggcag agtctcgatt accgcggacg agtccacgac cactgcctac    240

atggagctga gcagcccgag atctgaggac acgggcgtgt attattgtgc gggacgaagc    300

ccagacgatt attttggttc tcgtcgggac aactatcact acgggataga cgtctggggc    360

caagggacca cggtcaccgt ctcctcaggc ggtggtggat caggcggcgg aggatctggc    420

ggaggtggca gcggtggtgg aggcagtgaa attgtgatga cgcagtctcc atcctcattg    480

tctgcatctg taggagacag agtcaccatc acgtgtcggg cgagtcaggg cattggcaat    540

tatttagcct ggtttcagca gaaaccaggg aaagccccta agcccctgat ctttgctgca    600

tccaacttgc aaagtggggt cccatcaagg ttcagcggcg gtggatctgg gacagaattc    660

actctcacca tcaccggcct gcagcctgaa gattttgcaa cttattactg ccaacagtat    720

aattattacc ctcccacttt cggcggaggg accaaggtgg aaatcaaa                768
```

<210> SEQ ID NO 11
<211> LENGTH: 768
<212> TYPE: DNA
<213> ORGANISM: Artificial
<220> FEATURE:
<223> OTHER INFORMATION: Synthetically generated sequence (V_region)

<400> SEQUENCE: 11

-continued

```
caggtccagc tggtgcagtc tggggctgag gagaagaagc ctgggtcctc ggtgaaggtc     60

tcctgcaagg cctctggagg ccccctcagc gactatggtt tcagctgggt gcgactggcc    120

cctggacaag ggcttgagtg ggtgggaggg atcatcccta tgtttggaac accaaactac    180

gcacagaagt ttcagggcag agtctcgatt accgcggacg agtccacgac cactgcctac    240

atggagctga gcagcctgag atctgaggac acgggcgtgt attattgtgc gggacgaagc    300

ccagacgatt attttggttc tcgtcgggac aactatcact acgggataga cgtctggggc    360

caagggacca cggtcaccgt ctcctcaggc ggtggtggat caggcggcgg aggatctggc    420

ggaggtggca gcggtggtgg aggcagtgaa attgtgatga cgcagtctcc atcctcattg    480

tctgcatctg taggagacag agtcaccatc acgtgtcggg cgagtcaggg cattggcaat    540

tatttagcct ggtttcagca gaaaccaggg aaagccccta agcccctgat ctttgctgca    600

tccaacttgc aaagtggggt cccatcaagg ttcagcggcg gtggatctgg gacagaattc    660

actctcacca tcaccggcct gcagcctgag gattgtgcaa cttattactg ccaacagtat    720

aattattacc ctcccacttt cggcggaggg accaaggtgg aaatcaaa                 768
```

<210> SEQ ID NO 12
<211> LENGTH: 756
<212> TYPE: DNA
<213> ORGANISM: Artificial
<220> FEATURE:
<223> OTHER INFORMATION: Synthetically generated sequence (V_region)

<400> SEQUENCE: 12

```
gaggtgcagc tggtggagtc tgggggaggt ctggtcaagc ctgggggtc cctgagactc     60

tcctgtgcag cctctggatt caccttcagt agctatagca tgaactgggt ccgccaggct    120

ccagggaagg ggctggagtg ggtctcatcc attagtagta gtagtagtta catatactac    180

gcagactcag tgaagggccg attcaccatc tccagagaca acgccaagaa ctcactgtat    240

ctgcaaatga acagcctgag agccgaggac acggctgtgt attactgtgc gagaggatac    300

cgcggtagta gtggaaactg gtacttcgat ctctggggcc gtggcaccct ggtcaccgtc    360

tcctcaggcg gtggtggatc aggcggcgga ggatctggcg gaggtggcag ctggaggcag    420

tcagtctgct tgacgcagcc gccctcagtg tctggggccc cagggcagag ggtcaccatc    480

tcctgcactg ggagcagccc caacatcggg gcaggttatg atgtacactg gtaccagcaa    540

cttccaggaa ccgcccccga actcctcatc tatggtaacg acaaccggcc ctcaggggtc    600

cctgaccgat tctctggctc caagtctggc acctcagtct ccctggccat cactgggctc    660

caggctgagg atgaggctga ttattactgt cagtcctatg acaacagcct gagtgccaat    720

gcggttttcg gcggagggac caagctcacc gtccta                             756
```

<210> SEQ ID NO 13
<211> LENGTH: 756
<212> TYPE: DNA
<213> ORGANISM: Artificial
<220> FEATURE:
<223> OTHER INFORMATION: Synthetically generated sequence (V_region)

<400> SEQUENCE: 13

```
gaggtgcagc tggtggagtc tgggggaggc ctggtcaggc ctgggggtc cctgagactc     60

tcctgtgcag cctctggatt caccttcagt agctatagca tgaactgggt ccgccaggct    120

ccagggaagg ggctggagtg ggtctcatcc attagtagta gtagtagtta catatactac    180
```

-continued

```
gcagactcag tgaagggccg attcaccatc tccagagaca acgccaagaa ctcactgtat    240

ctgcaaatga acagcctgag agccgaggac acggctgtgt attactgtgc gagaggatac    300

cgcggtagta gtggaaactg gtacttcgat ctctggggcc gtggcaccct ggtcaccgtc    360

tcctcaggcg gtggtggatc aggcggcgga ggatctggcg gaggtggcag ctggaggcag    420

tcagtctgct tgacgcagcc gccctcagtg tctggggccc cagggcagag ggtcaccatc    480

tcctgcactg ggagcagccc caacatcggg gcaggttatg atgtacactg gtaccagcaa    540

cttccaggaa ccgcccccaa actcctcatc tatggtaacg acaaccggcc ctcaggggtc    600

cctgaccgat tctctggctc caagtctggc acctcagtct ccctggccat cactgggctc    660

caggctgagg atgaggctga ttattactgt cagtcctatg acaacagcct gagtgccaat    720

gcggttttcg gcggagggac caagctcacc gtccta                              756
```

<210> SEQ ID NO 14
<211> LENGTH: 252
<212> TYPE: PRT
<213> ORGANISM: Artificial
<220> FEATURE:
<223> OTHER INFORMATION: Synthetically generated sequence (DOMAIN)

<400> SEQUENCE: 14

```
Glu Val Gln Leu Val Glu Ser Gly Gly Gly Leu Val Arg Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Arg Gly Ser Ser Gly Asn Trp Tyr Phe Asp Leu Trp
            100                 105                 110

Gly Arg Gly Thr Leu Val Thr Val Ser Ser Gly Gly Gly Gly Ser Gly
        115                 120                 125

Gly Gly Gly Ser Gly Gly Gly Gly Ser Trp Arg Gln Ser Val Cys Leu
    130                 135                 140

Thr Gln Pro Pro Ser Val Ser Gly Ala Pro Gly Gln Arg Val Thr Ile
145                 150                 155                 160

Ser Cys Thr Gly Ser Ser Pro Asn Ile Gly Ala Gly Tyr Asp Val His
                165                 170                 175

Trp Tyr Gln Gln Leu Pro Gly Thr Ala Pro Lys Leu Leu Ile Tyr Gly
            180                 185                 190

Asn Asp Asn Arg Pro Ser Gly Val Pro Asp Arg Phe Ser Gly Ser Lys
        195                 200                 205

Ser Gly Thr Ser Val Ser Leu Ala Ile Thr Gly Leu Gln Ala Glu Asp
    210                 215                 220

Glu Ala Asp Tyr Tyr Cys Gln Ser Tyr Asp Asn Ser Leu Ser Ala Asn
225                 230                 235                 240

Ala Val Phe Gly Gly Gly Thr Lys Leu Thr Val Leu
                245                 250
```

-continued

<210> SEQ ID NO 15
<211> LENGTH: 252
<212> TYPE: PRT
<213> ORGANISM: Artificial
<220> FEATURE:
<223> OTHER INFORMATION: Synthetically generated sequence (DOMAIN)

<400> SEQUENCE: 15

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Arg Gly Ser Ser Gly Asn Trp Tyr Phe Asp Leu Trp
            100                 105                 110

Gly Arg Gly Thr Leu Val Thr Val Ser Ser Gly Gly Gly Gly Ser Gly
        115                 120                 125

Gly Gly Gly Ser Gly Gly Gly Gly Ser Trp Arg Gln Ser Val Cys Leu
    130                 135                 140

Thr Gln Pro Pro Ser Val Ser Gly Ala Pro Gly Gln Arg Val Thr Ile
145                 150                 155                 160

Ser Cys Thr Gly Ser Ser Pro Asn Ile Gly Ala Gly Tyr Asp Val His
                165                 170                 175

Trp Tyr Gln Gln Leu Pro Gly Thr Ala Pro Glu Leu Leu Ile Tyr Gly
            180                 185                 190

Asn Asp Asn Arg Pro Ser Gly Val Pro Asp Arg Phe Ser Gly Ser Lys
        195                 200                 205

Ser Gly Thr Ser Val Ser Leu Ala Ile Thr Gly Leu Gln Ala Glu Asp
    210                 215                 220

Glu Ala Asp Tyr Tyr Cys Gln Ser Tyr Asp Asn Ser Leu Ser Ala Asn
225                 230                 235                 240

Ala Val Phe Gly Gly Gly Thr Lys Leu Thr Val Leu
                245                 250
```

<210> SEQ ID NO 16
<211> LENGTH: 256
<212> TYPE: PRT
<213> ORGANISM: Artificial
<220> FEATURE:
<223> OTHER INFORMATION: Synthetically generated sequence (DOMAIN)

<400> SEQUENCE: 16

```
Gln Val Gln Leu Val Gln Ser Gly Ala Glu Glu Lys Lys Pro Gly Ser
1               5                   10                  15

Ser Val Lys Val Ser Cys Lys Ala Ser Gly Gly Pro Leu Ser Asp Tyr
            20                  25                  30

Gly Phe Ser Trp Val Arg Leu Ala Pro Gly Gln Gly Leu Glu Trp Val
        35                  40                  45

Gly Gly Ile Ile Pro Met Phe Gly Thr Pro Asn Tyr Ala Gln Lys Phe
    50                  55                  60
```

-continued

```
Gln Gly Arg Val Ser Ile Thr Ala Asp Glu Ser Thr Thr Thr Ala Tyr
65                  70                  75                  80

Met Glu Leu Ser Ser Leu Arg Ser Glu Asp Thr Gly Val Tyr Tyr Cys
                85                  90                  95

Ala Gly Arg Ser Pro Asp Asp Tyr Phe Gly Ser Arg Arg Asp Asn Tyr
            100                 105                 110

His Tyr Gly Ile Asp Val Trp Gly Gln Gly Thr Thr Val Thr Val Ser
        115                 120                 125

Ser Gly Gly Gly Gly Ser Gly Gly Gly Gly Ser Gly Gly Gly Gly Ser
    130                 135                 140

Gly Gly Gly Gly Ser Glu Ile Val Met Thr Gln Ser Pro Ser Ser Leu
145                 150                 155                 160

Ser Ala Ser Val Gly Asp Arg Val Thr Ile Thr Cys Arg Ala Ser Gln
                165                 170                 175

Gly Ile Gly Asn Tyr Leu Ala Trp Phe Gln Gln Lys Pro Gly Lys Ala
            180                 185                 190

Pro Lys Pro Leu Ile Phe Ala Ala Ser Asn Leu Gln Ser Gly Val Pro
        195                 200                 205

Ser Arg Phe Ser Gly Gly Gly Ser Gly Thr Glu Phe Thr Leu Thr Ile
    210                 215                 220

Thr Gly Leu Gln Pro Glu Asp Cys Ala Thr Tyr Tyr Cys Gln Gln Tyr
225                 230                 235                 240

Asn Tyr Tyr Pro Pro Thr Phe Gly Gly Gly Thr Lys Val Glu Ile Lys
                245                 250                 255


<210> SEQ ID NO 17
<211> LENGTH: 256
<212> TYPE: PRT
<213> ORGANISM: Artificial
<220> FEATURE:
<223> OTHER INFORMATION: Synthetically generated sequence  (DOMAIN)

<400> SEQUENCE: 17

Gln Val Gln Leu Val Gln Ser Gly Ala Glu Val Lys Lys Pro Gly Ser
1               5                   10                  15

Ser Val Lys Val Ser Cys Lys Ala Ser Gly Gly Pro Leu Ser Asp Tyr
            20                  25                  30

Gly Phe Ser Trp Val Arg Leu Ala Pro Gly Gln Gly Leu Glu Trp Val
        35                  40                  45

Gly Gly Ile Ile Pro Met Phe Gly Thr Pro Asn Tyr Ala Gln Lys Phe
    50                  55                  60

Gln Gly Arg Val Ser Ile Thr Ala Asp Glu Ser Thr Thr Thr Ala Tyr
65                  70                  75                  80

Met Glu Leu Ser Ser Pro Arg Ser Glu Asp Thr Gly Val Tyr Tyr Cys
                85                  90                  95

Ala Gly Arg Ser Pro Asp Asp Tyr Phe Gly Ser Arg Arg Asp Asn Tyr
            100                 105                 110

His Tyr Gly Ile Asp Val Trp Gly Gln Gly Thr Thr Val Thr Val Ser
        115                 120                 125

Ser Gly Gly Gly Gly Ser Gly Gly Gly Gly Ser Gly Gly Gly Gly Ser
    130                 135                 140

Gly Gly Gly Gly Ser Glu Ile Val Met Thr Gln Ser Pro Ser Ser Leu
145                 150                 155                 160

Ser Ala Ser Val Gly Asp Arg Val Thr Ile Thr Cys Arg Ala Ser Gln
                165                 170                 175
```

-continued

Gly Ile Gly Asn Tyr Leu Ala Trp Phe Gln Gln Lys Pro Gly Lys Ala
180 185 190

Pro Lys Pro Leu Ile Phe Ala Ala Ser Asn Leu Gln Ser Gly Val Pro
195 200 205

Ser Arg Phe Ser Gly Gly Gly Ser Gly Thr Glu Phe Thr Leu Thr Ile
210 215 220

Thr Gly Leu Gln Pro Glu Asp Phe Ala Thr Tyr Tyr Cys Gln Gln Tyr
225 230 235 240

Asn Tyr Tyr Pro Pro Thr Phe Gly Gly Gly Thr Lys Val Glu Ile Lys
245 250 255

<210> SEQ ID NO 18
<211> LENGTH: 253
<212> TYPE: PRT
<213> ORGANISM: Artificial
<220> FEATURE:
<223> OTHER INFORMATION: Synthetically generated sequence (DOMAIN)

<400> SEQUENCE: 18

Glu Val Gln Leu Val Glu Ser Gly Gly Gly Leu Ile Gln Pro Gly Gly
1 5 10 15

Ser Leu Arg Leu Ser Cys Gly Ala Ser Gly Phe Thr Phe Ser Thr Ser
20 25 30

Trp Met Thr Trp Val Arg Gln Ala Pro Gly Lys Gly Leu Glu Trp Val
35 40 45

Ala Thr Ile Gly Gln Asp Gly Ser Gln Gln Tyr Tyr Ala Asp Ser Val
50 55 60

Lys Gly Arg Phe Thr Val Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Ala Leu Asp Asp Ser Ala Gly Trp Phe Glu Phe Asp Phe Trp
100 105 110

Gly Gln Gly Thr Leu Val Thr Val Ser Ser Gly Gly Gly Gly Ser Gly
115 120 125

Gly Gly Gly Ser Gly Gly Gly Gly Ser Gly Gly Gly Gly Ser Asn Phe
130 135 140

Met Leu Thr Gln Pro His Ser Val Ser Glu Ala Pro Gly Lys Thr Val
145 150 155 160

Thr Ile Ser Cys Thr Gly Ser Ser Ser Asn Ile Gly Ala Gly Tyr Asp
165 170 175

Val His Trp Tyr Gln Gln Leu Pro Gly Ser Ala Pro Lys Val Leu Ile
180 185 190

Tyr Gly Asn Asn Asn Arg Pro Ser Gly Val Pro Asp Arg Phe Ser Gly
195 200 205

Ser Lys Ser Gly Thr Ser Ala Ser Leu Ala Ile Thr Ala Phe Gln Ala
210 215 220

Glu Asp Glu Ala Asp Tyr Tyr Cys Gln Ser Tyr Asp Ser Ser Leu Ser
225 230 235 240

Gly Val Val Phe Gly Gly Gly Thr Gln Leu Thr Val Leu
245 250

<210> SEQ ID NO 19
<211> LENGTH: 253
<212> TYPE: PRT
<213> ORGANISM: Artificial
<220> FEATURE:

-continued

<223> OTHER INFORMATION: Synthetically generated sequence (DOMAIN)

<400> SEQUENCE: 19

```
Glu Val Gln Leu Val Glu Ser Gly Gly Gly Leu Ile Gln Pro Gly Gly
1               5                   10                  15

Ser Leu Arg Leu Ser Cys Gly Ala Ser Gly Phe Thr Phe Ser Thr Ser
            20                  25                  30

Trp Met Thr Trp Val Arg Gln Ala Pro Gly Lys Gly Leu Glu Trp Val
        35                  40                  45

Ala Thr Ile Gly Pro Asp Gly Ser Gln Gln Tyr Tyr Val Asp Ser Val
    50                  55                  60

Lys Gly Arg Phe Thr Val Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ala Leu Asp Asp Ser Ala Gly Trp Phe Glu Phe Asp Phe Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Ser Gly Gly Gly Gly Ser Asn Phe
    130                 135                 140

Met Leu Thr Gln Pro His Ser Val Ser Glu Ala Pro Gly Lys Thr Val
145                 150                 155                 160

Thr Ile Ser Cys Thr Gly Ser Ser Ser Asn Ile Gly Ala Gly Tyr Asp
                165                 170                 175

Val His Trp Tyr Gln Gln Leu Pro Gly Ser Ala Pro Lys Val Leu Ile
            180                 185                 190

Tyr Gly Asn Asn Asn Arg Pro Ser Gly Val Pro Asp Arg Phe Ser Gly
        195                 200                 205

Ser Lys Ser Gly Thr Ser Ala Ser Leu Ala Ile Thr Ala Phe Gln Ala
    210                 215                 220

Glu Asp Glu Ala Asp Tyr Tyr Cys Gln Ser Tyr Asp Ser Ser Leu Ser
225                 230                 235                 240

Gly Val Val Phe Gly Gly Gly Thr Gln Leu Thr Val Leu
                245                 250
```

<210> SEQ ID NO 20
<211> LENGTH: 253
<212> TYPE: PRT
<213> ORGANISM: Artificial
<220> FEATURE:
<223> OTHER INFORMATION: Synthetically generated sequence (DOMAIN)

<400> SEQUENCE: 20

```
Glu Val Gln Leu Val Glu Ser Gly Gly Gly Leu Ile Gln Pro Gly Gly
1               5                   10                  15

Ser Leu Arg Leu Ser Cys Val Ala Ser Gly Phe Thr Phe Ser Thr Ser
            20                  25                  30

Trp Met Thr Trp Val Arg Gln Ala Pro Gly Lys Gly Leu Glu Trp Val
        35                  40                  45

Ala Thr Ile Gly Gln Asp Gly Ser Gln Gln Tyr Tyr Val Asp Ser Val
    50                  55                  60

Lys Gly Arg Phe Thr Val Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95
```

-continued

```
Ala Arg Ala Leu Asp Asp Ser Ala Gly Trp Phe Glu Phe Asp Phe Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Ser Gly Gly Gly Gly Ser Asn Phe
    130                 135                 140

Met Leu Thr Gln Pro His Ser Val Ser Glu Ala Pro Gly Lys Thr Val
145                 150                 155                 160

Thr Ile Ser Cys Thr Gly Ser Ser Ser Asn Ile Gly Ala Gly Tyr Asp
                165                 170                 175

Val His Trp Tyr Gln Gln Leu Pro Gly Ser Ala Pro Lys Val Leu Ile
            180                 185                 190

Tyr Gly Asn Asn Asn Arg Pro Ser Gly Val Pro Asp Arg Phe Ser Asp
        195                 200                 205

Ser Lys Ser Gly Thr Ser Ala Ser Leu Ala Ile Thr Ala Phe Gln Ala
    210                 215                 220

Glu Asp Glu Ala Asp Tyr Tyr Cys Gln Ser Tyr Asp Ser Ser Leu Ser
225                 230                 235                 240

Gly Val Val Phe Gly Gly Gly Thr Gln Leu Thr Val Leu
                245                 250


<210> SEQ ID NO 21
<211> LENGTH: 256
<212> TYPE: PRT
<213> ORGANISM: Artificial
<220> FEATURE:
<223> OTHER INFORMATION: Synthetically generated sequence  (DOMAIN)

<400> SEQUENCE: 21

Gln Val Gln Leu Val Gln Ser Gly Ala Glu Val Lys Lys Pro Gly Ser
1               5                   10                  15

Ser Val Lys Val Ser Cys Lys Ala Ser Gly Gly Pro Leu Ser Asp Tyr
            20                  25                  30

Gly Phe Ser Trp Val Arg Leu Ala Pro Gly Gln Gly Leu Glu Trp Val
        35                  40                  45

Gly Gly Ile Ile Pro Met Phe Gly Thr Pro Asn Tyr Ala Gln Lys Phe
    50                  55                  60

Gln Gly Gly Val Ser Ile Thr Ala Asp Glu Ser Thr Thr Thr Ala Tyr
65                  70                  75                  80

Met Glu Leu Ser Ser Leu Arg Ser Glu Asp Thr Gly Val Tyr Tyr Cys
                85                  90                  95

Ala Gly Arg Ser Pro Asp Asp Tyr Phe Gly Ser Arg Arg Asp Asn Tyr
            100                 105                 110

His Tyr Gly Ile Asp Val Trp Gly Gln Gly Thr Thr Val Thr Val Ser
        115                 120                 125

Ser Gly Ser Gly Gly Ser Gly Gly Gly Gly Ser Gly Gly Gly Gly Ser
    130                 135                 140

Gly Gly Gly Gly Ser Glu Ile Val Met Thr Gln Ser Pro Ser Ser Leu
145                 150                 155                 160

Ser Ala Ser Val Gly Gly Arg Val Thr Ile Thr Cys Arg Ala Ser Gln
                165                 170                 175

Gly Ile Gly Asn Tyr Leu Ala Trp Phe Gln Gln Lys Pro Gly Lys Ala
            180                 185                 190

Pro Lys Pro Leu Ile Phe Ala Ala Ser Asn Leu Gln Ser Gly Val Pro
        195                 200                 205
```

-continued

Ser Arg Phe Ser Gly Gly Gly Ser Gly Thr Glu Phe Thr Leu Thr Ile
    210                 215                 220

Thr Gly Leu Gln Pro Glu Asp Phe Ala Thr Tyr Tyr Cys Gln Gln Tyr
225                 230                 235                 240

Asn Tyr Tyr Pro Pro Thr Phe Gly Gly Gly Thr Lys Val Glu Ile Lys
                245                 250                 255

<210> SEQ ID NO 22
<211> LENGTH: 253
<212> TYPE: PRT
<213> ORGANISM: Artificial
<220> FEATURE:
<223> OTHER INFORMATION: Synthetically generated sequence (DOMAIN)

<400> SEQUENCE: 22

Glu Val Gln Leu Val Glu Ser Gly Gly Gly Leu Ile Gln Pro Gly Gly
1               5                   10                  15

Ser Leu Arg Leu Ser Cys Gly Ala Ser Gly Phe Thr Phe Ser Thr Ser
            20                  25                  30

Trp Met Ala Trp Val Arg Gln Ala Pro Gly Lys Gly Leu Glu Trp Val
        35                  40                  45

Ala Thr Ile Gly Gln Asp Gly Ser Gln Gln Tyr Tyr Ala Asp Ser Val
    50                  55                  60

Lys Gly Arg Phe Thr Val Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ala Leu Asp Asp Ser Ala Gly Trp Phe Glu Phe Asp Phe Trp
            100                 105                 110

Gly Pro Gly Thr Leu Val Thr Val Ser Ser Gly Gly Gly Gly Pro Gly
        115                 120                 125

Gly Gly Gly Ser Gly Gly Gly Gly Ser Gly Gly Gly Gly Ser Asp Phe
    130                 135                 140

Met Leu Thr Gln Pro His Ser Val Ser Glu Ala Pro Gly Lys Thr Val
145                 150                 155                 160

Thr Ile Ser Cys Thr Gly Ser Ser Ser Asn Ile Gly Ala Gly Tyr Asp
                165                 170                 175

Val His Trp Tyr Gln Gln Leu Pro Gly Ser Ala Pro Lys Val Leu Ile
            180                 185                 190

Tyr Gly Asn Ser Asn Arg Pro Ser Gly Val Pro Asp Arg Phe Ser Gly
        195                 200                 205

Ser Lys Ser Gly Thr Ser Ala Ser Pro Ala Ile Thr Ala Phe Gln Ala
    210                 215                 220

Glu Asp Glu Ala Asp Tyr Tyr Cys Gln Ser Tyr Asp Ser Ser Leu Ser
225                 230                 235                 240

Gly Val Val Phe Gly Gly Gly Thr Gln Leu Thr Val Leu
                245                 250

<210> SEQ ID NO 23
<211> LENGTH: 253
<212> TYPE: PRT
<213> ORGANISM: Artificial
<220> FEATURE:
<223> OTHER INFORMATION: Synthetically generated sequence (DOMAIN)

<400> SEQUENCE: 23

Glu Val Gln Leu Val Glu Ser Gly Gly Gly Leu Ile Gln Pro Gly Gly

-continued

```
1               5                   10                  15

Ser Leu Arg Leu Ser Cys Gly Ala Ser Gly Phe Thr Phe Ser Thr Ser
            20                  25                  30

Trp Met Ala Trp Val Arg Gln Ala Pro Gly Lys Gly Leu Glu Trp Val
        35                  40                  45

Ala Thr Ile Gly Gln Asp Gly Ser Gln Gln Tyr Tyr Ala Asp Ser Val
    50                  55                  60

Lys Gly Arg Phe Thr Val Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ala Leu Asp Asp Ser Ala Gly Trp Phe Glu Phe Asp Phe Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Ser Gly Gly Gly Gly Ser Asn Phe
    130                 135                 140

Thr Leu Thr Gln Pro His Ser Val Ser Glu Ala Pro Gly Arg Thr Val
145                 150                 155                 160

Thr Ile Ser Cys Thr Gly Ser Ser Ser Asn Ile Gly Ala Gly Tyr Asp
                165                 170                 175

Val His Trp Tyr Gln Gln Leu Pro Gly Ser Ala Pro Lys Val Leu Ile
            180                 185                 190

Tyr Gly Asn Ser Asn Arg Pro Ser Gly Val Pro Asp Arg Phe Ser Gly
        195                 200                 205

Ser Lys Ser Gly Thr Ser Ala Ser Leu Ala Ile Thr Ala Phe Gln Ala
    210                 215                 220

Glu Asp Glu Ala Asp Tyr Tyr Cys Gln Ser Tyr Asp Ser Ser Leu Ser
225                 230                 235                 240

Gly Glu Val Phe Gly Gly Gly Thr Gln Leu Thr Val Leu
                245                 250


<210> SEQ ID NO 24
<211> LENGTH: 253
<212> TYPE: PRT
<213> ORGANISM: Artificial
<220> FEATURE:
<223> OTHER INFORMATION: Synthetically generated sequence  (DOMAIN)

<400> SEQUENCE: 24

Glu Val Gln Leu Val Glu Ser Gly Gly Gly Leu Ile Gln Pro Gly Gly
1               5                   10                  15

Ser Leu Arg Leu Ser Cys Gly Ala Ser Gly Phe Thr Phe Ser Thr Ser
            20                  25                  30

Trp Met Ala Trp Val Arg Gln Ala Pro Gly Lys Gly Leu Glu Trp Val
        35                  40                  45

Ala Thr Ile Gly Gln Asp Gly Ser Gln Gln Tyr Tyr Ala Asp Ser Val
    50                  55                  60

Glu Gly Arg Phe Thr Val Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ala Leu Asp Asp Ser Ala Gly Trp Phe Glu Phe Asp Phe Trp
            100                 105                 110

Gly Gln Gly Thr Leu Val Thr Val Ser Ser Gly Gly Gly Gly Ser Gly
```

-continued

```
        115                 120                 125

Gly Gly Gly Ser Gly Gly Gly Gly Ser Gly Gly Gly Gly Ser Asn Phe
    130                 135                 140

Thr Leu Thr Gln Pro His Ser Val Ser Glu Ala Pro Gly Arg Thr Val
145                 150                 155                 160

Thr Ile Ser Cys Thr Gly Ser Ser Ser Asn Ile Gly Ala Gly Tyr Asp
                165                 170                 175

Val His Trp Tyr Gln Gln Pro Pro Gly Ser Ala Pro Lys Val Leu Thr
            180                 185                 190

Tyr Gly Asn Ser Asn Arg Pro Ser Gly Val Pro Asp Arg Phe Ser Gly
        195                 200                 205

Ser Lys Ser Gly Thr Ser Ala Ser Pro Ala Ile Thr Ala Phe Gln Ala
    210                 215                 220

Glu Asp Glu Ala Asp His Tyr Cys Gln Ser Tyr Asp Ser Ser Leu Ser
225                 230                 235                 240

Gly Glu Ala Phe Gly Gly Gly Thr Gln Leu Thr Val Leu
                245                 250


<210> SEQ ID NO 25
<211> LENGTH: 263
<212> TYPE: PRT
<213> ORGANISM: Artificial
<220> FEATURE:
<223> OTHER INFORMATION: Synthetically generated sequence  (DOMAIN)

<400> SEQUENCE: 25

Glu Val Gln Leu Val Glu Ser Gly Gly Gly Leu Ile Gln Pro Gly Gly
1               5                   10                  15

Ser Leu Arg Leu Ser Cys Gly Ala Ser Gly Phe Thr Phe Ser Thr Ser
            20                  25                  30

Trp Met Ala Trp Val Arg Gln Ala Pro Gly Lys Gly Leu Glu Trp Val
        35                  40                  45

Ala Thr Ile Gly Gln Asp Gly Ser Gln Gln Tyr Tyr Ala Asp Ser Val
    50                  55                  60

Lys Gly Arg Phe Thr Val Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ala Leu Asp Asp Ser Ala Gly Trp Phe Glu Phe Asp Phe Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Ser Gly Gly Gly Gly Ser Asn Phe
    130                 135                 140

Thr Leu Thr Gln Pro His Ser Val Ser Glu Ala Pro Gly Arg Thr Val
145                 150                 155                 160

Thr Ile Ser Cys Thr Gly Ser Ser Ser Asn Ile Gly Ala Gly Tyr Asp
                165                 170                 175

Val His Trp Tyr Gln Gln Leu Pro Gly Ser Ala Pro Lys Val Leu Thr
            180                 185                 190

Tyr Gly Asn Ser Asn Arg Pro Ser Gly Val Pro Asp Arg Phe Ser Gly
        195                 200                 205

Ser Lys Ser Gly Thr Pro Ala Ser Pro Ala Ile Thr Ala Phe Gln Ala
    210                 215                 220

Glu Asp Glu Ala Asp Tyr Tyr Cys Gln Ser Tyr Asp Ser Ser Leu Ser
```

-continued 225 230 235 240

Gly Glu Val Phe Gly Gly Gly Thr Gln Leu Thr Val Leu Pro Asn Ser
245 250 255

Ser Thr Gln Leu Thr Val Leu
260

<210> SEQ ID NO 26
<211> LENGTH: 253
<212> TYPE: PRT
<213> ORGANISM: Artificial
<220> FEATURE:
<223> OTHER INFORMATION: Synthetically generated sequence (DOMAIN)

<400> SEQUENCE: 26

Glu Val Gln Leu Val Glu Ser Gly Gly Gly Leu Ile Gln Pro Gly Gly
1 5 10 15

Ser Leu Arg Leu Ser Cys Gly Ala Ser Gly Phe Thr Phe Ser Thr Ser
20 25 30

Trp Met Ala Trp Val Arg Gln Ala Pro Gly Lys Gly Leu Glu Trp Val
35 40 45

Ala Thr Ile Gly Gln Asp Gly Ser Gln Gln Tyr Tyr Ala Asp Ser Val
50 55 60

Lys Gly Arg Phe Thr Val Ser Arg Asp Asn Ala Lys Asn Ser Leu Cys
65 70 75 80

Leu Gln Met Asn Ser Leu Arg Ala Glu Asp Thr Ala Val Tyr Tyr Cys
85 90 95

Ala Arg Ala Leu Asp Asp Ser Ala Gly Trp Phe Glu Phe Asp Phe Trp
100 105 110

Gly Gln Gly Thr Leu Val Thr Val Ser Ser Gly Gly Gly Gly Ser Gly
115 120 125

Gly Gly Gly Ser Gly Gly Gly Gly Ser Gly Gly Gly Gly Ser Asn Phe
130 135 140

Thr Pro Thr Gln Pro His Ser Val Ser Glu Ala Pro Gly Arg Thr Val
145 150 155 160

Thr Ile Ser Cys Thr Gly Ser Ser Ser Asn Ile Gly Ala Gly Tyr Asp
165 170 175

Val His Trp Tyr Gln Gln Leu Pro Gly Ser Ala Pro Asn Val Leu Ile
180 185 190

Tyr Gly Asn Ser Asn Arg Pro Ser Gly Val Pro Asp Arg Phe Ser Gly
195 200 205

Pro Lys Ser Gly Thr Pro Ala Ser Pro Ala Ile Thr Ala Phe Gln Ala
210 215 220

Glu Asp Glu Ala Asp Tyr Tyr Cys Gln Ser Tyr Asp Ser Ser Leu Ser
225 230 235 240

Gly Glu Val Phe Gly Gly Gly Thr Gln Leu Thr Val Leu
245 250

<210> SEQ ID NO 27
<211> LENGTH: 297
<212> TYPE: PRT
<213> ORGANISM: Enterovirus 71 strain TW/1743/98
<220> FEATURE:
<221> NAME/KEY: PEPTIDE
<222> LOCATION: (1)..(297)

<400> SEQUENCE: 27

Gly Asp Arg Val Ala Asp Val Ile Glu Ser Ser Ile Gly Asp Ser Val
1 5 10 15

-continued

```
Ser Lys Ala Leu Thr Pro Ala Leu Pro Ala Pro Thr Gly Pro Asp Thr
            20                  25                  30

Gln Val Ser Ser His Arg Leu Asp Thr Gly Lys Val Pro Ala Leu Gln
        35                  40                  45

Ala Ala Glu Ile Gly Ala Ser Ser Asn Ala Ser Asp Glu Ser Met Ile
    50                  55                  60

Glu Thr Arg Cys Val Leu Asn Ser His Ser Thr Ala Glu Thr Thr Leu
65                  70                  75                  80

Asp Ser Phe Phe Ser Arg Ala Gly Leu Val Gly Glu Ile Asp Leu Pro
                85                  90                  95

Leu Lys Gly Thr Thr Asn Pro Asn Gly Tyr Ala Asn Trp Asp Ile Asp
            100                 105                 110

Ile Thr Gly Tyr Ala Gln Met Arg Arg Lys Val Glu Leu Phe Thr Tyr
        115                 120                 125

Met Arg Phe Asp Ala Glu Phe Thr Phe Val Ala Cys Thr Pro Thr Gly
    130                 135                 140

Arg Val Val Pro Gln Leu Leu Gln Tyr Met Phe Val Pro Pro Gly Ala
145                 150                 155                 160

Pro Lys Pro Asp Ser Arg Asp Ser Leu Ala Trp Pro Thr Ala Thr Asn
                165                 170                 175

Pro Ser Val Phe Val Lys Ser Ser Asp Pro Pro Ala Gln Val Ser Val
            180                 185                 190

Pro Phe Met Ser Pro Ala Ser Ala Tyr Gln Trp Phe Tyr Asp Gly Tyr
        195                 200                 205

Pro Thr Phe Gly Glu His Lys Gln Glu Lys Asp Leu Glu Tyr Gly Ala
    210                 215                 220

Cys Pro Asn Asn Met Met Gly Thr Phe Ser Val Arg Thr Val Gly Ser
225                 230                 235                 240

Ser Lys Ser Glu Tyr Ser Leu Val Ile Arg Ile Tyr Met Arg Met Lys
                245                 250                 255

His Val Arg Ala Trp Ile Pro Arg Pro Met Arg Asn Gln Asn Tyr Leu
            260                 265                 270

Phe Lys Ser Asn Pro Asn Tyr Ala Gly Asp Ser Ile Lys Pro Thr Gly
        275                 280                 285

Thr Ser Arg Thr Ala Ile Thr Thr Leu
    290                 295
```

<210> SEQ ID NO 28
<211> LENGTH: 22
<212> TYPE: DNA
<213> ORGANISM: Artificial
<220> FEATURE:
<223> OTHER INFORMATION: Synthetically generated sequence (primer)

<400> SEQUENCE: 28
tcctcctgcg aagctgctga ct 22

<210> SEQ ID NO 29
<211> LENGTH: 31
<212> TYPE: DNA
<213> ORGANISM: artificial
<220> FEATURE:
<223> OTHER INFORMATION: Synthetically generated sequence (primer)

<400> SEQUENCE: 29
cactcttcca tggatatcct acagacaggc a 31

-continued

```
<210> SEQ ID NO 30
<211> LENGTH: 35
<212> TYPE: DNA
<213> ORGANISM: artificial
<220> FEATURE:
<223> OTHER INFORMATION: Synthetically generated sequence  (primer)

<400> SEQUENCE: 30

tcctcttcta aggagagtgg trattgctgt gcgac                            35


<210> SEQ ID NO 31
<211> LENGTH: 33
<212> TYPE: DNA
<213> ORGANISM: artificial
<220> FEATURE:
<223> OTHER INFORMATION: Synthetically generated sequence  (primer)

<400> SEQUENCE: 31

tgctctagag ccaccatgaa gcatctgtgg ttc                              33


<210> SEQ ID NO 32
<211> LENGTH: 21
<212> TYPE: DNA
<213> ORGANISM: artificial
<220> FEATURE:
<223> OTHER INFORMATION: Synthetically generated sequence  (primer)

<400> SEQUENCE: 32

tcatcattta cccggagaca c                                           21


<210> SEQ ID NO 33
<211> LENGTH: 33
<212> TYPE: DNA
<213> ORGANISM: artificial
<220> FEATURE:
<223> OTHER INFORMATION: Synthetically generated sequence  (primer)

<400> SEQUENCE: 33

tcccccgggg ccaccatgag ggtccccgct cag                              33


<210> SEQ ID NO 34
<211> LENGTH: 27
<212> TYPE: DNA
<213> ORGANISM: artificial
<220> FEATURE:
<223> OTHER INFORMATION: Synthetically generated sequence  (primer)

<400> SEQUENCE: 34

ggaagatctt caacactctc ccctgtt                                     27
```

RECOMBINANT ENTEROVIRUS 71 NEUTRALIZING ANTIBODIES AND APPLICATIONS THEREOF

The present application hereby claims priority under 35 U.S.C. §119 on Republic of China application number 094115151 filed May 11, 2005, the entire contents of which is hereby incorporated herein by reference.

BACKGROUND OF THE INVENTION

1. Field of the Invention

This invention relates to peptides possessing biological activity, particularly for use in vaccines for diseases caused by enterovirus. The invention further relates to anti-viral therapeutics, particularly recombinant human anti-EV71 monoclonal antibodies. The invention further relates to application of said antibodies for use in therapy, surgery and diagnosis of EV71 infection.

2. Description of Prior Art

Hand, foot and mouth disease (HFMD) is generally a mild, self-limited disease that primarily affects infants and young children. The infection of enterovirus 71 (EV71) is the second most common cause of HFMD (CDC report, Aug. 7, 1998; CDC report, Aug. 11, 1998). The infection of EV71 is often complicated with severe neurological manifestations including viral (aseptic) meningitis, encephalitis, and a polio-like paralysis.

EV71 was first isolated and characterized in 1969 (Schmidt et al., 1974, *J. Infect. Dis.* 129:304). Many reports of EV71 outbreaks were filed around the world before 1998, mostly in Southeast Asia (Lam, 1998, *Emerg. Infect. Dis.* 4:145; WHO report, June, 1998; WHO report, July, 1998). The World Health Organization had reported Hong-Kong, Malaysia, and Taiwan as epidemic areas. The most serious outbreak of all epidemics was the one in Taiwan during April-July 1998, resulting in about 320 cases with severe complications and at least 73 deaths (Wu et al., 1999, *Emerg. Infect. Dis,* 5:458; Wang et al., 1999, *Clin. Infect. Dis.* 29(1):184; Komatsu et al., 1999, *Pediatr. Neurol.* 20:17).

The period from infection of EV71 to the onset of symptoms in infants is 3 to 6 days. Fever is often the first symptom of HFMD. One or two days after the fever begins, sores develop in the mouth and often become ulcers later. The skin rash develops for 1 to 2 days, usually located on the palms of hands and soles of feet. Most patients recover in 1 to 2 weeks (WHO report, June, 1998; CDC report, Aug. 7, 1998). Some cases, mostly children younger than 3 years old, however, develop severe complications. They exhibited a short (2-4 days) febrile illness, followed by a sudden deterioration, and died within 12 to 24 hours (CDC report, Aug. 07, 1998). It is not clear why most infected children spontaneously recover, while some succumb to the infection and develop complication at a very fast course.

It has been reported that EV71-neutralizing IgM is produced in monkey 14 to 20 days after infection (Hashinmoto and Hagiwara, 1982, *Neuropathol. Appl. Neurobiol.* 8:149; Hashinmoto and Hagiwara, 1983, *Acta. Neuropathol* 60:266). It is suggested that the sudden death, which occurs at about day 7, of some infected children is due to their inability of producing sufficient neutralizing antibodies in time. Currently there is no effective agent or treatment to counter the infection of EV71. Available treatments of HFMD are often symptomatic, directed to relieving fever, headache, and malaise. Managing complications of the disease complications has become the most important concern in clinical caring (CDC report, Aug. 11, 1998). Therefore, an effective treatment to inhibit viral propagation and to clear virus particles is highly desirable.

The technique for producing monoclonal antibodies (mAbs) using the hybridoma methodology was invented in 1975 (Cottona and Milstein, 1973, *Nature* 244:42; Kohler and Milstein, 1975, *Nature* 256:495). In the past two decades, a number of mAbs for therapeutic applications have been developed. These mAbs recognize critical molecules or pathogens of a specific disease, and mediate immune mechanisms to eliminate them. Up to 2001, eleven murine gene-modified mAbs have reached the market, and 3 await regulatory approval (Glennie and Johnson, 2000, *Immunol. Today* 21:403; Ezzell, 2001, *Sci. Am.* 285:34).

Synagis is one of the successful monoclonal antibodies designed to recognize the virus-neutralizing site of respiratory syncytial virus (RSV), the F protein, and thus inhibit the RSV infection (Malley et al., 1998, *J. Infect. Dis.* 178:1555; Marchetti et al., 1999, *Clin. Ther.* 21:752.). Such notable success has stimulated wide academic and industrial interests of developing monoclonal antibodies as therapeutic agents. More than 100 mAbs are now being tested in human and have shown encouraging results.

EV71 is a positive single stranded RNA virus. The viral RNA is encapsidated by four structural proteins: viral protein 1 (VP1), VP2, VP3, and VP4, which are produced by post-translational cleavages of a common naked protein precursor. Of these viral proteins, VP1 has been suggested to be mainly responsible for attachment of enteroviruses to target cell (Graham et al., 1989, *J. Gen. Virol.* 70:625) and hence harbors the main antigenic determinants for virus neutralization (Pfaff et al., 1988, *J. Virol.* 62:2033; Rueckert, 1990, Virology/Lippin-cott-Raven, p. 507). Immunological studies with different enterovirus strains have indicated that the dominant epitopes of several monoclonal neutralizing antibodies (mAbs) are located on VP1 (Philip et al., 1986, *J. Gene. Virol.* 67:1283; Tapani et al., 1993, *J. Clin. Microbiol.* 31:1083; Hyppia et al., 1997, *J. Gene. Virol.* 78:1).

Several groups have identified short segments of VP1 as crucial elements in inducing protective immunity and have designed oligopeptides for possible applications (U.S. Pat. No. 4,694,071, U.S. Pat. No. 4,751,083, U.S. Pat. No. 4,875,643). Pregnant ICR mice immunized with VP1 proteins or DNA of EV71 have also been found to produce sufficient neutralizing antibodies to protect newborn mice from EV71 infection (Wu, C. N. et al., 2002, *Vaccine* 20:895).

Although EV71 is a genetically diverse, rapidly evolving virus, the 3 genotypes of VP1 proteins of all isolated strains from more than 6 countries, including the prototype strain BrCr-CA-70, are at least 94% identical to one another (Brown et al., 2000, *J. Viol.* 74:12003). During the outbreak of EV71 in Taiwan, many clinical isolates were obtained and characterized. It was found that the VP1 proteins found in different regions of Taiwan have almost identical sequences. Comparing amino acid sequences of VP1 in GenBank showed that VP1 proteins share high sequence similarity between different isolates (>96%) and more than 98.9% identity within the same genotype (Wang et al., 2002, *J. Clin. Microbiol.* 40:10; Shih et al., 2000, *Virus Res.* 68:127). These data indicate that VP1 is very conserved and does not undergo significant mutations in infected individuals. Thus EV71 is a potent neutralizing site of EV71 and a suitable antigenic target.

In the past 15 years, the methodology of generating antibody has been greatly improved with the advent of antibody engineering and transgenic technologies. A new generation of antibodies, fully human monoclonal antibodies, has been produced for clinical applications. The best known methods of developing human monoclonal antibodies include displaying human $V_H$-$V_L$ single chain (scFv) libraries on phage surface, preparing antibodies in transgenic mice, harboring genes of human heavy chain/light chain immunoglobulins and producing antibodies with hybridomas made with human myeloma cells (Soderlind et al., 1993, *Biotechnol.* 11:503; Vaughan et al., 1998, *Nat. Biotechnol.* 16:535; Karpas et al., 2001, *Proc. Natl. Acad. Sci. USA* 98:1799). Experimental data shows that these mAbs have much reduced immunogenicity, longer half-lives and enhanced immune activities in human patients.

Recently, a high throughput generation/screening system of human antibody repertoire has been constructed in yeast (for example, U.S. Pat. No. 6,406,863, the disclosure of which is hereby incorporated, in its entirety, by reference). As compared with a phage displayed library, antibodies produced in yeast perform protein folding after being expressed, and should be more functionally relevant to human antibodies then those expressed on phage surface. In addition, screening for antibody-antigen interaction can be conveniently carried out in yeast using a yeast two-hybrid method, which could save much time than conventional strategies described above. Hence, the yeast two-hybrid system provides an efficient and economical way to screen for fully human antibodies Another advantage of the yeast antibody library is the high incidence of homologous recombination in yeast. DNA shuffling between the VH and VL sequences further increases the complexity of the antibody library and also increases the binding affinity of selected scFv clones after maturation. Anti-EV71 neutralizing antibodies with higher affinity could be obtained via antibody maturation.

BRIEF SUMMARY OF THE INVENTION

In this invention, we have prepared human antibodies specific for EV71 by using a combination of yeast two-hybrid system and an array of antibody affinity maturation techniques. A library of single-chain antibodies was constructed using the $V_H$ and $V_L$ gene segments in B-lymphocytes of healthy individuals. The single-chain antibodies can be fused with the activation domain of transcription factor of GAL1 promoter for convenient screening and cloning. After screening, the selected $V_H$ and $V_L$ genes can be placed into a human IgG expression cassette. The recombinant genes will then be expressed using transfectoma technology for producing large quantities of recombinant antibodies.

BRIEF DESCRIPTION OF THE DRAWINGS

FIG. 1 illustrates a yeast two-hybrid system for high throughput screening of antibodies. EV71 vp1: capsid protein VP1 of enterovirus 71, scFv: single chain Fv fragment of antibody, DNA-BD: DNA binding domain, AD: transcription-activating domain, and GAL1 UAS: upstream activating sequence of GAL1. (A) The DNA-BD/EV71 vp1 protein binds to the GAL1 upstream activating sequence but cannot activate transcription without the AD. (B) The AD/scFv library protein cannot localize to the UAS and thus does not activate transcription. (C) Interaction between the EV71 vp1 and scFv library encoded regions of the two hybrid proteins reconstitutes GAL1 function and results in reporter gene expression.

FIG. 2 illustrates the antigen-association specificity of EV71 VP1 positive clones. Upper: parental clones of G338, G235 and G234; middle: parental clones of G333, G334 and G335; and lower: parental clones of G621, G622, G623, G624 and G625.

FIG. 6 illustrates BIAcore 2000 Affinity Assay for binding of scFv to recombinant VP1.

FIG. 7 illustrates the neutralizing activity of scFvs. (A) Selected scFv clones against EV71 type B. (B) Selected scFv clones against EV71 type C.

FIG. 8 illustrates the use of a plaque reduction assay to assess the neutralizing activity of scFvs. (A) EV71-B-type, and (B) EV71-C-type.

FIG. 10 illustrates assessing Neutralizing Activity of full G625 with plaque reduction assay. (A) G625 against EV71 type B, and (B) G625 against EV71 type C.

DETAILED DESCRIPTION OF THE INVENTION

Antibodies

Figure 3:
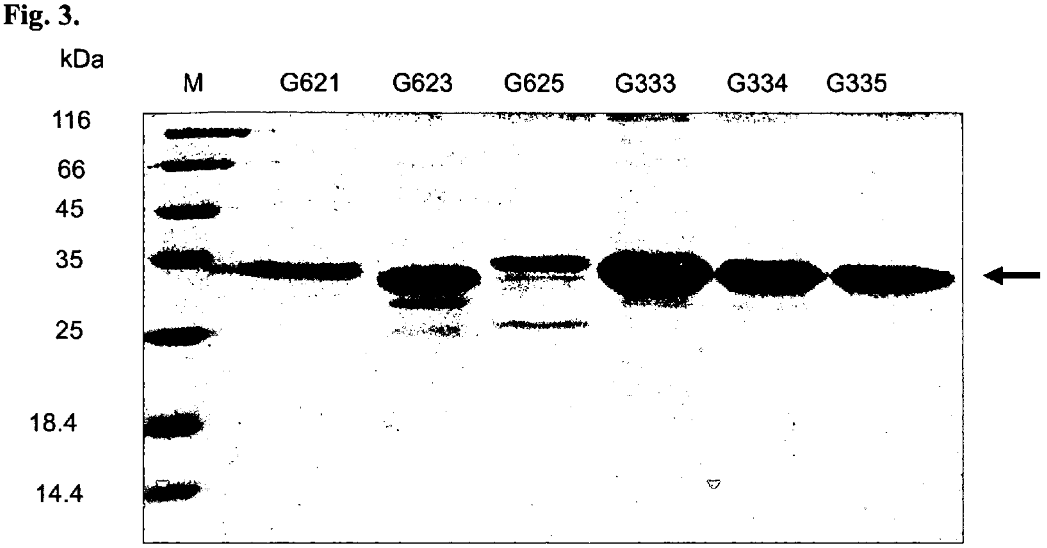
FIG. 3 illustrates purification of candidate scFvs. The arrowhead indicates the purified scFv.

In a first embodiment, the invention provides an antibody specific to VP1 of EV71. The term “antibody” is used herein to include complete antibodies (i.e., antibodies having two heavy and two light chains) as well as fragments of antibodies which contain an antigen binding site, such as Fab, F(ab')2, Fv and single chain Fv (scFv) fragments. However, the antibody according to the invention is preferably an scFv antibody. A scFv is composed of a variable light chain (VL), a variable heavy chain (VH), and a flexible linker linking VL and VH. scFvs are able to bind antigen and can be rapidly produced in bacteria.

This invention provides an antibody against enterovirus 71 comprising the amino acid sequence shown in SEQ ID NO: 14, 15, 16, 17, 18, 19, 20, 21, 22, 23, 24, 25, or 26 or functionally active homologues thereof. In a better embodiment, the antibody comprising the amino acid sequence shown in SEQ ID NO: 26, can be used to design other antibodies of similar specificity. The antibody is encoded from polynucleotides comprising the nucleotide sequences shown in SEQ ID NOS: 1, 2, 3, 4, 5, 6, 7, 8, 9, 10, 11, 12, or 13. The antibody of this invention is a human monoclonal antibody. The antibody of this invention is a single chain Fv (scFv) antibody. Further, the amino acid sequence is used to produce a bispecific antibody. The bispecific antibody comprises two variable regions, and one of the regions is selected from one of the group consisting of SEQ ID NOS: 14, 15, 16, 17, 18, 19, 20, 21, 22, 23, 24, 25 and 26. In a better embodiment, both variable regions have the sequences selected from the described group.

The antibody according to the invention has an anti-virus agent or a detectable label attached thereto. The anti-virus agent or the detectable label is selected from one group consisting of chemotherapeutic agent, radioisotope, enzyme, prodrug, and cytokine. This allows the antibody to target the agent or the detectable label to the virus and hence allows damage/destruction or detection of the virus. Thus the antibody is used for therapy or surgery, such as used in a method of treatment of the human or animal body by therapy or surgery (e.g., radioimmunoguided surgery), or in a method of diagnosis practiced on the human or animal body. In particular, the antibody is suitable for use in treatment by surgery or therapy of an enterovirus infection, or in diagnosis of an enterovirus infection.

The anti-virus agent linked to the antibody may be any agent that destroys or damages a virus to which the antibody has bound or in the environment of the cell to which the antibody has bound. For example, the anti-virus agent may be a toxic agent such as a chemotherapeutic agent or a radioisotope, or an enzyme, a prodrug or a cytokine.

Suitable chemotherapeutic agents are known to those skilled in the art and include anthracyclines (e.g., daunomycin and doxorubicin), methotrexate, vindesine, neocarzinostatin, cis-platinum, chlorambucil, cytosine arabinoside, 5-fluorouridine, melphalan, ricin and calicheamicin.

Suitable radioisotopes for use as anti-virus agents are also known to those skilled in the art.

The anti-virus agent that is attached to the antibody may also be an enzyme that activates a prodrug. This allows activation of an inactive prodrug to its active, cytotoxic form at the infected site and is called "antibody-directed enzyme prodrug therapy" (ADEPT). In clinical practice, the antibody-enzyme conjugate is administered to the patient and allowed to localize in the region of the infection to be treated. The prodrug is then administered to the patient so that conversion to the cytotoxic drug is localized in the region of the infection to be treated under the influence of the localized enzyme.

The detectable label attached to the antibody may be an imaging agent for site imaging such as a short-lived radioisotope, for example $^{111}$In, $^{125}$I or $^{99}$mTc.

An antibody according to the invention containing a detectable label is useful for radioimmunoguided surgery (RIGS) in addition to being useful for diagnosis. RIGS comprises administering a labeled antibody to a patient and thereafter surgically removing any tissue to which the antibody binds. Thus, the labeled antibody guides the surgeon towards tissue.

Further, the detectable label is used for detecting or quantifying enterovirus. The method for detecting or quantifying enterovirus comprises: (a) contacting a sample with the antibody, (b) detecting or quantifying the labeled antibody, wherein the enterovirus is whole viral particle or VP1 subunit and the sample is detected or quantified in vitro. The antibody according to the invention can be used for in vitro detection or quantification of VP1. For example, the antibody may be used for enzyme-linked immunoassay (ELISA), Western blotting or in situ detection of enterovirus in a tissue sample. Thus, the antibody may be used in a method for detecting or quantifying VP1 in a sample, the method comprises:

(a) contacting the sample with a labeled antibody, and (b) detecting or quantifying labeled antibody bound to any VP1 in the sample.

Typically, an ELISA method for detecting or quantifying VP1 in a sample using an antibody according the invention comprises:

(c) immobilizing an unlabelled antibody on a solid support according to the invention, (d) adding the sample such that any enterovirus in the sample is captured by the unlabelled antibody, (e) adding a labeled antibody according to the invention, and (f) detecting or quantifying any bound labeled antibody.

An antibody of the invention may also be employed histologically for in situ detection or quantification of VP1, for example by immunofluorescence or immunoelectron microscopy. Detection or determination in situ may be accomplished by removing a tissue specimen from a patient and allowing a labeled antibody to bind to any VP1 in the specimen. Through use of such a procedure, it is possible to find not only the presence of VP1 but also its spatial distribution.

An antibody of the invention may be used to purify VP1. Conventional methods of purifying an antigen using an antibody may be used. Such methods include immunoprecipitation and immunoaffinity column methods. In an immunoaffinity column method, an antibody in accordance with the invention is coupled to the inert matrix of the column and a sample containing VP1 is passed down the column, such that VP1 is retained. The VP1 is then eluted.

The sample containing VP1 used in the above detection, determination and purification methods may be a tissue specimen or a cell extract from a patient. Alternatively, the sample may be one produced as a result of recombinant DNA procedures, e.g., an extract of a culture of host cells expressing VP1.

The detectable label attached to the antibody for in vitro use may be a radioisotope (e.g. $^{32}$p or $^{35}$S), a biotin (which may be detected by avidin or steptavidin conjugated to peroxidase), a digoxigenin, an alkaline phosphatase or a fluorescent label (e.g., fluorescein or rhodamine).

This invention also provides a method for obtaining an antibody according to this invention, comprising: (a) selecting a yeast expressing said antibody from a yeast library, (b) culturing the yeast under conditions that said antibody is expressed, and (c) recovering said antibody from the culture. The yeast library is made by (a) preparing DNA segments of $V_H$ and $V_L$ from peripheral blood pools by RT-PCR, (b) joining VH and VL coding regions by a sequence encoding a linker, and (c) transforming yeasts with vectors containing the joined regions.

The vector is used for the replication and expression of DNA encoding an antibody according to the invention. The vector is selected from a group consisting of plasmid, virus and phage vectors, which is provided with an origin of replication, optionally a promoter for the expression of the said DNA and operably linked to said DNA. "Operably linked" refers to a juxtaposition wherein the promoter and the antibody coding sequence are in a relationship permitting the coding sequence to be expressed under the control of the promoter. The vector may also comprise a regulator of the promoter. The vector may contain one or more selectable marker genes, for example an ampicillin resistance gene in the case of a bacterial plasmid or a neomycin resistance gene for a mammalian vector. The vector may be used in vitro, for example for the production of RNA corresponding to the DNA, or for the use of transfecting or transforming a host cell.

The present invention also provides a process for producing the antibody, comprising: (a) culturing a host cell in conditions that the antibody is expressed, (b) recovering the antibody from the culture, wherein the host cell is transformed or transfected for expressing the antibody according to this invention. The host cell can be bacterial, yeast, insect or mammalian cell, dependent on the compatibility with the vector. In better embodiment, the host cell is yeast.

The invention includes a pharmaceutical composition used for therapy, comprising an antibody according to this invention, and a pharmaceutically acceptable carrier or diluent, wherein the antibody has an anti-virus agent or detectable label attached thereto. The pharmaceutical composition is used for therapy of enterovirus 71. In clinical use, the antibody will normally be administered parenterally, e.g., intravenously or intraperitonealy. Thus, the pharmaceutical composition is normally one that is suitable for parenteral (e.g., intravenous or intraperitoneal) administration. Such a composition conveniently contains the antibody and isotonic saline or bicarbonate as diluent. The dose of antibody will ultimately be at the discretion of the physician, who will take account of factors such as the type of therapy or diagnosis, the weight, condition and age of the patient. Suitable doses of antibody are known in the art. A suitable dose may be from 0.01 to 100 mg, preferably from 0.1 to 10 mg for a human patient. The antibody according to the invention can be used in a similar way to known enterovirus.

The following examples are offered by way of illustration and not by way of limitation.

EXAMPLES

Example 1

Construction of scFv Library, VP1 Fusion Protein and Screening for Antibody Leads Using Yeast Two-Hybrid System DNA segments of human antibody $V_H$ and $V_L$ were prepared from peripheral blood cells of pooled blood samples by RT-PCR with sets of oligonucleotide primers to amplify the cDNA of human heavy and light chains variable domains (Orlandi et al., 1989, *Proc. Natl. Acad. Sci. USA* 86:3833). The primers for gene amplification of $V_H$ and $V_\kappa$ have been designed based on the consensus sequence of different Ig gene families (primer sequences refer to U.S. Pat. No. 6,406,863). The amplified segments were further linked with a spacer/linker sequence encoded (Gly-Gly-Gly-Gly-Ser)$_4$ (SEQ ID NO:35) to form single-chain antibodies (scFv).

In order to perform high throughput screening of antibodies, the prepared scFv libraries were adopted as tester proteins in a yeast two-hybrid system (U.S. Pat. No. 6,406,863). Each tester protein was a fusion protein comprised of a scFv protein linked to an activation domain (AD) of a transcription activator. The yeast cells were also modified to express a recombinant fusion protein comprising a DNA-binding domain (BD) of the transcription activator and the target antigen, VP1 of EV71 (SEQ ID NO: 27). The yeast cells were also modified to express a reporter gene whose expression is under the control of a specific DNA binding site. Upon binding of the scFv antibody from the library to the target antigen, the AD was brought to close proximity of BD, thereby causing transcriptional activation of the reporter gene (LacZ/HIS3) downstream of a specific DNA binding site to which the BD binds (FIG. 1). Positive clones could be selected by histidine depleted media plates and expression level could be measured by ONPG assay.

To prepare the gene segments of target antigen, viruses of EV71 type B (TW/1743) and type C (TW/2086) were isolated from patients' specimens and propagated in Vero or RD cells. After amplification, virus particles were purified by sucrose gradient centrifugation as described in Abraham and Colonno, 1984, *J. Virol.* 57:340; Smyth et al., 1993, *J. Mol. Biol.* 230:667. Virus RNA was extracted with virus RNA purification kit according to the manufacturer's instructions (Qiagen Co., USA). The VP1 gene segments from both genotypes were amplified by RT-PCR and were cloned into the downstream of DNA-binding domain (BD) of the transcription activator. Viral RNA was extracted from the culture fluid of the neu-infected cells using a commercially-available kit (QIAamp viral RNA mini kit, Qiagen Inc., Santa Clara, Calif.). The first strand cDNA was synthesized using reverse transcriptase (Promega, USA) and a primer (SEQ ID NO: 28) that was complementary to the 3' end of the viral gene encoding capsid protein VP1 (Wu et al., 2002, *Vaccine* 20:895).

The double-stranded cDNA encoding the entire VP1 protein was amplified by polymerase chain reaction (PCR) for 35 cycles (94° C.×1 min, 55° C.×1 min and 72° C.×2 min), using Pfu DNA polymerase (Stratagene, USA) and a pair of primers Envp1F (SEQ ID NO: 29) and Envp1R (SEQ ID NO: 30), which were designed according to the known viral gene sequence encoding the N- and C-termini of VP1. The PCR amplicon of VP1 was introduced into pcDNA3 plasmid (Invirtogen, USA) at EcoR I site.

The constructed scFv expression vector and the VP1-expression vector were introduced into different strains of haploid yeast cells (U.S. Pat. No. 6,406,863). These scFv expression vectors are introduced to yeast cells by direct mating between two strains of haploid yeast cells. The two strains of haploid yeast cells, alpha-type strain and a-type strain, contained the scFv expression vector and the VP1-expression vector, respectively. The two strains were mated to produce a diploid yeast cell containing both expression vectors. The haploid yeast strain containing the target antigen expression vector also contained the reporter gene located downstream of the specific DNA binding site. After mating of the two strains of haploid yeast cells, if the scFv antibody from the library binds to the target VP1, the AD is brought to close proximity to BD, causing transcriptional activation of the respective reporter gene.

The yeast clones containing scFv antibodies with binding affinity to the target VP1 were selected based on the intensity of the reporter gene and other selectable markers. The plasmids encoding these scFv antibody leads can be isolated and further characterized. Ten parental clones were selected. Affinity of those clones were further improved by mutagenic PCR, additional thirteen maturated clones were selected (DNA SEQ ID NOS: 1-13, Protein SEQ ID NOS: 14-26). The antigen-association specificity of some EV71 VP1 positive clones in the yeast two-hybrid system were compared with 6 control baits (FIG. 2).

Example 2

Purification of Candidate scFvs

To confirm the antigen specificity of selected scFv clones from the yeast two-hybrid system, the DNA segments of scFv clones were subcloned into an *E. coli* expression vector, pET27b+ (Novagen Co., Germany) (refer to vector maps), and introduced into BL21 (pLys) strain of *E. coli*. After 1 mM IPTG induction for 4 hrs at 37° C., scFv protein modified with a $(His)_6$ tag and a HSV tag, was expressed and precipitated in the inclusion body. The inclusion bodies were resolved in 6M Guanidine-HCl buffer (5 mM imidazole, 0.5M NaCl, 20 mM Tris-HCl) with shaking for overnight at 4° C. After centrifugation (16000×g, 20 min), the clear supernatant was collected, filtered with a 0.45 μm syringe filter, and applied to a 2 ml Ni-NTA resin affinity column. The column was washed with 10 ml of Wash Buffer I (6M Guanidine-HCl buffer, 5 mM imidazole, 0.5M NaCl, 20 mM Tris-HCl) and Wash Buffer II (6M Guanidine-HCl buffer, 20 mM imidazole, 0.5M NaCl, 20 mM Tris-HCl). Finally, scFv was eluted with Elute buffer (6M Guanidine-HCl buffer, 50 mM imidazole, 0.5M NaCl, 20 mM Tris-HCl) (FIG. 3). The purified scFv proteins were dialyzed with renaturing buffer containing 0.5M L-arginine (100 mM Tris, pH=8.0, 1 mM EDTA, 1 mM DTT, 20% glycerol, 0.5% Sarkosyl, 0.5M L-arginine) for 2 days to restore protein folding (Lin et al., 2001, *Anal. Biochem.* 294: 44).

Example 3

Purification of VP1

Figure 4:
FIG. 4 illustrates SDS-PAGE of Ni affinity purified recombinant EV71 VP1. The arrowhead indicates the eluted EV71 VP1-$His_6$.

To characterize the activity of expressed scFv, VP1 gene segment in the yeast expression vector was subcloned into a pETblue2 vector (Novagen Co., Germany) (refer to vector maps) to prepare the recombinant VP1 protein, which was modified with a $(His)_6$ tag in C-terminal. The procedures of VP1 protein expression, purification, and refolding were similar to that of scFv proteins (FIG. 4).

Example 4

Examination of the Binding Specificity of scFvs with ELISA

Figure 5:
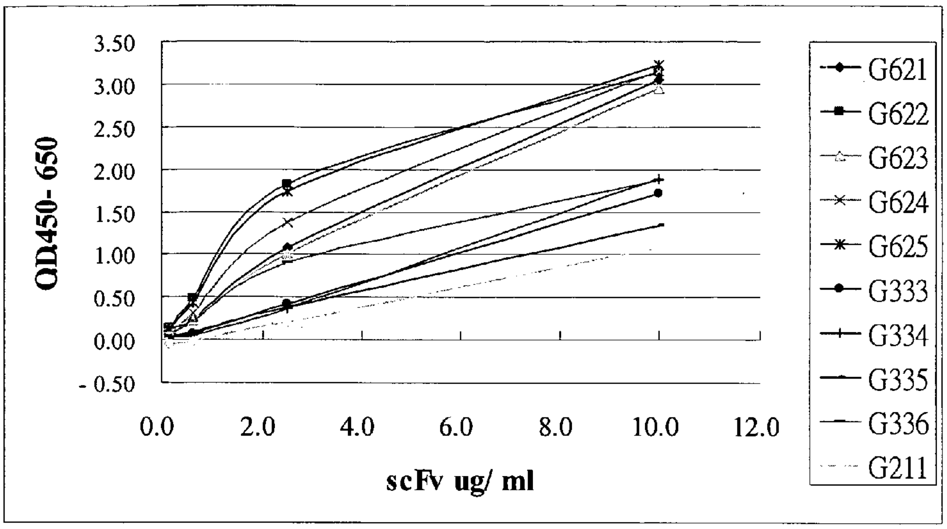
FIG. 5 illustrates Using ELISA to examine binding specificity of scFvs.

Selected clones were subjected to ELISA to examine their binding with recombinant VP1 protein (FIG. 5). Purified VP1 was coated on 96-well plates at 500 ng/well in 0.1M $NaCO_3$, pH=9.6 and incubated at 4° C. overnight. Coated wells were blocked by 300 μl/well of 5% Skim milk in PBS at 37° C. for 1 hour. Plates were washed five times with 400 μl/well of PBS with 0.05% Tween-20. Individual purified scFv antibody was diluted to 0.5 μg/ml, 1.0 μg/ml, 1.5 μg/ml or 2.0 μg/ml by 0.1% gelatin in PBS and 100 μl/well was added to coated plates. The incubation was carried out at 37° C. for 2 hours. All wells were aspirated and washed five times with 400 μl/well of PBS and 0.05% Tween-20. Second antibody mouse anti-HSV tag was added at 20 ng/well and incubated at 37° C. for 1 hour. Then all wells were aspirated and washed five times with 400 μl/well of PBS and 0.05% Tween-20. Bound antibodies were detected by horseradish peroxidase conjugated anti-mouse IgG antibody (1:5000 diluted 1 mg/ml Antibody solution, 100 μl/well) at 37° C. for 1 hour. Then all wells were aspirated and washed five times with 400 μl/well of PBS and 0.05% Tween-20. Finally, wells were developed by 100 μl/well of TMB substrate and absorbencies were measured at 450 nm with a reference at 650 nm. The binding specificity of the selected clones was further characterized using a cell-based ELISA to screen EV71 virus-infected Vero cells as the antigen. It has been reported that VP1 protein was expressed and accumulated in the cytosol of infected Vero cells 8-12 hrs after virus infection. At this stage, the infected cell were still attached to the bottom of culture wells. EV71-infected Vero cells were fixed and an assay similar to typical ELISA was used to examine the specific reactivity of selected scFv (Data not shown). Binding affinity to the recombinant VP1 protein was measured by BIAcore 2000 (Pharmacia Co., USA) (FIG. 6). 200 μM of selected scFv proteins were coupled onto Ni-NTA chips (Pharmacia Co., USA). Different concentration of VP1 proteins (50 nM to 1000 nM) were flowed through the chip and the binding curves were diagramed with BIAcore program. The association curve and dissociation curve of different concentrations of VP1 were plotted and the affinity of scFv is simulated according to the plots.

Example 5

Assessing the Neutralizing Activity of scFVs

The purified scFv proteins were co-cultured with virions to assay their neutralizing activities (Baxt et al., 1984, *J. Virol.* 51:298; Wiley et al., 1990, *Viral Immunol.* 3:137). $2\times10^4$ cells/well (human rhabdomyosarcoma, RD cell line) were seeded into 96-well plates one day before neutralizing assay. On the next day, two-fold serial dilutions of scFv proteins ($2^{-1}$~$2^{-10}$) were incubated with virus m.o.i.=$10^{-3}$ (multiplicity of infection) at 37° C. for 1 hr and then plated onto monolayers of RD cells in Dulbecco's Modified Eagle's Medium (DMEM) containing 2% fetal bovine serum for 3 days. The resultant cultures were fixed with 10% formalin and survival cells were stained with 1% crystal violet. The neutralizing activity of scFv was measured as the optical density of each well at 570 nm. Samples were assayed in triplicates. The $IC_{50}$ of scFv was estimated as the concentration of scFv required to inhibit 50% of the EV71 infectivity. Two scFv clones, scFv-334 and scFv-336 were assayed and an irrelevant clone, scFv-74, was included as a negative control. The neutralizing results showed that scFv-334 and scFv-336 could neutralize EV71 specifically and the IC50 was 3 μg/ml and 5 μg/ml, respectively (FIG. 7).

Example 6

Assessing the Neutralizing Activity of scFvs with Plaque Reduction Assay

EV71 virus particles (200 virus particles) were mixed with dilutions of scFv proteins or PBS control for 1 hr at 37° C., and then added to confluent monolayers of RD cells (in 6-well plate) in duplicated or triplicated for another 1 hr for virus absorption. After washing off the unbound virus particles, cells were cultured in medium containing 0.3% agarose at 37° C. 5% $CO_2$ incubator for 4 days. The numbers of plaques were determined after cells were fixed and stained with crystal violet. Eight scFv clones were assayed (scFv-G333, scFv-G334, scFv-G335, scFv-G336, scFv-G621, scFv-G622, scFv-G623, and scFv-G625) at 5 μg/ml against EV71 B-type (FIG. 8A) and EV71 C-type (FIG. 8B). It was found that antibodies from scFv clones reduced the numbers of plaque colonies for about 10% to 50% compared to the PBS control.

Example 7

Producing Full Antibodies with Baculovirus Expression System

Figure 9:
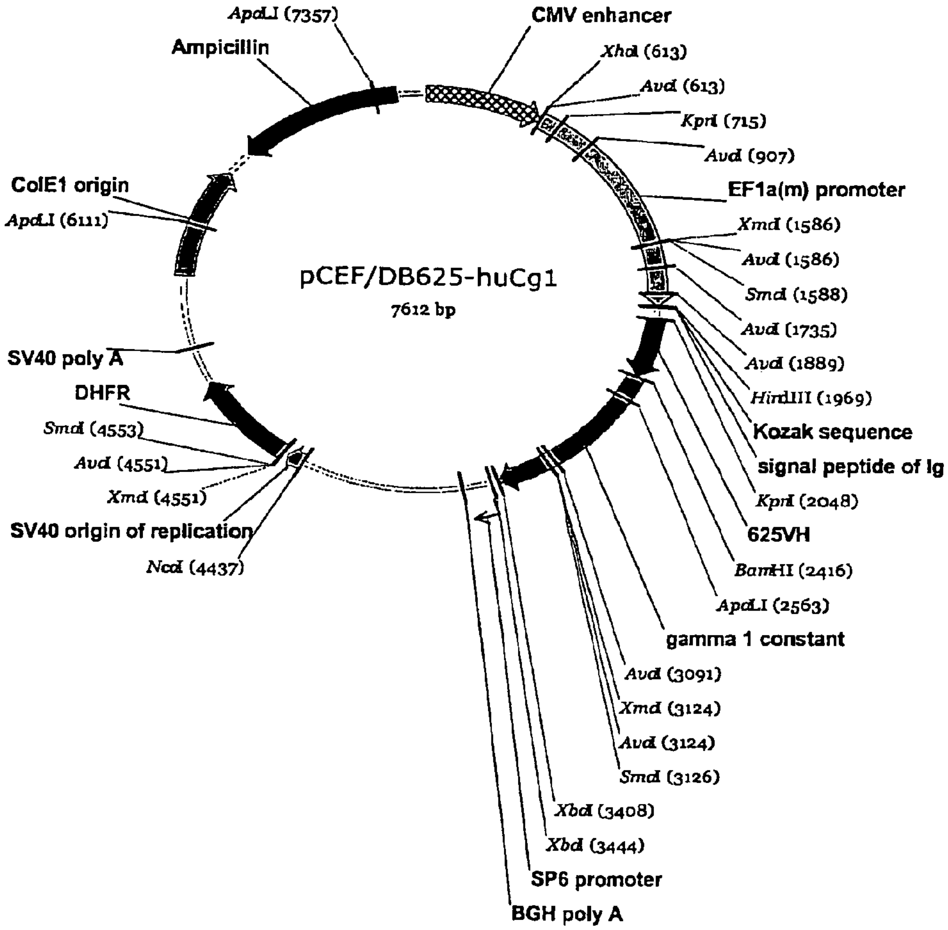
FIG. 9 illustrates construction of full G625 antibody recombinant baculovirus. (A) G625 Heavy Chain Construct (pCEF/DB625-huCg1), (B) G625 Light Chain Construct (pCEF/DB625-huCk), and (C) Baculovirus Transfer Vector (pAcDB3-G625Cg1Ck).

To produce full antibody, the IgG heavy chain was composed of IgG heavy chain signal peptide, scFv-G625 heavy chain variable region, and IgGγ1 constant region (pCEF/DB625-huCg1). The IgG light chain was composed of IgG κ light chain signal peptide, scFv-G625 light chain variable region, and IgGκ constant region (pCEF/DB625-huCk). G625 heavy chain was amplified by polymerase chain reaction (PCR) for 30 cycles (94° C.×30 sec, 60° C.×30sec and 72° C.×2 min), using ThermalAce DNA polymerase (Invitrogen, USA) and a pair of primers H625F (SEQ ID NO: 31) and H625R (SEQ ID NO: 32). The amplified heavy chain fragments were cloned in the baculovirus donor vector pAcDB3 (Pharmigen, USA) with Xba I and Stu I. The resulted plasmid was pAcDB3-G625Cr1. G625 light chain was amplified by polymerase chain reaction (PCR) for 30 cycles (94° C.×30 sec, 60° C.×30 sec and 72° C.×2 min), using ThermalAce DNA polymerase (Invitrogen, USA) and a pair of primers SmaLK (SEQ ID NO: 33) and L625R (SEQ ID NO: 34). The amplified light chain fragments were cloned in the pAcDB3-G625Cr1 with Xma I and Bgl II and resulted the plasmid pAcDB3-G625Cr1Ck (FIG. 9).

Recombinant baculovirus was prepared according to the user's manual of BaculoGold Expression System (Pharmigen, USA). Sf9 cells, grown in suspension in serum-free medium (Gibco), were infected at a m.o.i. of 10 with the recombinant baculovirus and incubated for 72 hours at 27° C. Cells were harvested by centrifugation at 1000×g for 10 min, washed twice with 1×PBS, and then lysed with 1×PBS, 1 mM PMSF and 1% Tween 20 on ice for 20 min. Clear supernatant was collected by centrifugation at 20000×g for 20 min and purified by Protein A affinity chromatography. The column with 1 ml of Protein A resin (HiTrap rProteinA 1 ml, Pharmacia, USA) was equilibrated with 10 ml of 1×PBS, loaded the clear supernatant, washed with 10 ml of 0.1M Glycine pH=4.5, and eluted with 0.1M Glycine pH=3.0. Eluted fractions were pooled and dialyzed against Dialysis buffer (10 mM HEPES, 150 mM KCl, 1 mM EDTA, 50% Glycerol, pH=8.0).

The neutralizing activity of full G625 antibody was determined by plaque reduction assay mentioned previously. Dilutions of purified full G625 antibody (1, 5, and 10 μg/ml), 10 μg/ml human IgG (Sigma, USA), and Dialysis Buffer were assayed. It was found that antibodies of full G625 (5 μg/ml) reduced the numbers of plaques about 75% for B type virus (FIG. 10A) and 50% for C type virus (FIG. 10B) compared to the control. The plaque numbers of human IgG and Dialysis buffer showed no significant differences compared with the virus only control.

These results suggest that the infectivity and hence the propagation of EV71 in the infected host cells can be blocked by certain monoclonal antibodies that are specific to VP1 of EV71.

---

What is claimed is:

1. An antibody against enterovirus 71 comprising an amino acid sequence including SEQ ID NO: 26.

2. A nucleotide sequence for encoding the antibody of claim 1, comprising SEQ ID NO: 13.

3. The antibody according to claim 1, wherein the antibody is a human monoclonal antibody.

4. The antibody according to claim 1, wherein the antibody is a single chain Fv (scFv) antibody.

5. The antibody according to claim 1, wherein the antibody is a bi-specific antibody.

6. The antibody according to claim 5, wherein the bi-specific antibody comprises two variable regions, one of which is selected from a group consisting of SEQ ID NOS: 14, 15, 16, 17, 18, 19, 20, 21, 22, 23, 24, and 25, and the other comprises SEQ ID NO: 26.

7. The antibody according to claim 1, wherein the antibody has a detectable or quantifiable label attached thereto.

8. The antibody according to claim 7, wherein detectable or quantifiable label is selected from a group consisting of chemotherapeutic agents, radioisotopes, enzymes, prodrugs, and cytokines.

9. A method for obtaining an antibody according to claim 1, comprising: (a) selecting a yeast expressing said antibody from a yeast library, (b) culturing the yeast under the conditions that said antibody is expressed, and (c) recovering said antibody from the culture.

10. The method according to claim 9, wherein the yeast library is made by (a) preparing DNA segments of VH and VL from peripheral blood pools by RT-PCR, (b) joining VH and VL coding regions by a sequence encoding a linker, and (c) transforming yeasts with vectors containing the joined regions.

11. The method according to claim 10, wherein the vector is used for replication and expression of DNA encoding a single chain Fv (scFv) antibody.

12. The method according to claim 11, wherein the vector is selected from a group consisting of plasmids, viruses and phage vectors.

13. A process for producing an antibody according to claim 1, comprising: (a) culturing a host cell under conditions that the antibody is expressed; and (b) recovering the antibody from the culture, wherein the host cell is transformed or transfected for expressing the antibody according to claim 1.

14. The process according to claim 13, wherein the host cell is selected from a group consisting of bacteria, yeast, insect cells and mammalian cells.

15. A pharmaceutical composition used for therapy of enterovirus 71, comprising: an antibody according to claim 1; and a pharmaceutically acceptable carrier or diluent.

* * * * *